United States Patent
Seow et al.

(10) Patent No.: US 12,114,882 B2
(45) Date of Patent: Oct. 15, 2024

(54) SURGICAL STAPLER FEATURES FOR STAPLING VARIABLE THICKNESS TISSUE

(71) Applicant: Cilag GmbH International, Zug (CH)

(72) Inventors: Christopher Q. Seow, Cincinnati, OH (US); Michael J. Vendely, Lebanon, OH (US); Mark S. Zeiner, Mason, OH (US); Jason M. Rector, Maineville, OH (US); Shannon L. Jones, Cincinnati, OH (US); Andréas N. Ward, Cincinnati, OH (US); Adam D. Hensel, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/704,094

(22) Filed: Mar. 25, 2022

(65) Prior Publication Data
US 2023/0301675 A1   Sep. 28, 2023

(51) Int. Cl.
*A61B 17/064*   (2006.01)
*A61B 17/00*   (2006.01)
(Continued)

(52) U.S. Cl.
CPC ........ *A61B 17/29* (2013.01); *A61B 17/00234* (2013.01); *A61B 17/0684* (2013.01);
(Continued)

(58) Field of Classification Search
CPC .......................... A61B 17/064; A61B 17/0682
(Continued)

(56) References Cited

U.S. PATENT DOCUMENTS

| 5,810,855 A | 9/1998 | Rayburn et al. |
| 7,380,696 B2 | 6/2008 | Shelton, IV et al. |

(Continued)

FOREIGN PATENT DOCUMENTS

| EP | 2090248 A2 | 8/2009 |
| EP | 3150134 A1 | 4/2017 |

(Continued)

OTHER PUBLICATIONS

International Search Report and Written Opinion dated Aug. 2, 2023, for International Application No. PCT/IB2023/052793, 20 pages.

(Continued)

*Primary Examiner* — Thanh K Truong
*Assistant Examiner* — Patrick B Fry
(74) *Attorney, Agent, or Firm* — Frost Brown Todd LLP

(57) ABSTRACT

A surgical instrument includes a first and second jaw actuatable between an open and closed position, a buttress assembly having a compressible material, and a fastener assembly associated with the second jaw. The fastener assembly and the buttress assembly may cooperatively grasp tissue while the first and second jaws are in the closed position. The fastener assembly includes a deck defining a plurality of openings and a plurality of fasteners each housed within a respective opening of the plurality of openings. Each fastener can actuate out of the respective opening and into the buttress assembly. Each fastener includes a first leg having a piercing tip, and an attachment feature associated with the first leg. The attachment feature can engage the buttress assembly to couple the first leg with the buttress assembly without bending a portion of the first leg associated with the piercing tip.

18 Claims, 26 Drawing Sheets

(51) Int. Cl.
  *A61B 17/068* (2006.01)
  *A61B 17/072* (2006.01)
  *A61B 17/29* (2006.01)
(52) U.S. Cl.
  CPC .. *A61B 17/072* (2013.01); *A61B 2017/07214* (2013.01); *A61B 2017/07242* (2013.01); *A61B 2017/2927* (2013.01)
(58) Field of Classification Search
  USPC ...................................................... 227/176.1
  See application file for complete search history.

(56) References Cited

U.S. PATENT DOCUMENTS

| | | | |
|---|---|---|---|
| 7,845,533 B2 * | 12/2010 | Marczyk | A61B 17/105 227/181.1 |
| 8,034,396 B2 * | 10/2011 | Kapiamba | A61L 24/043 528/319 |
| 8,210,411 B2 | 7/2012 | Yates et al. | |
| 8,408,439 B2 | 4/2013 | Huang et al. | |
| 8,453,914 B2 | 6/2013 | Laurent et al. | |
| 9,186,142 B2 | 11/2015 | Fanelli et al. | |
| 9,271,706 B2 * | 3/2016 | Stopek | A61L 27/52 |
| 9,364,233 B2 * | 6/2016 | Alexander, III | A61B 46/17 |
| 9,517,065 B2 | 12/2016 | Simms et al. | |
| 9,622,746 B2 | 4/2017 | Simms et al. | |
| 9,649,110 B2 * | 5/2017 | Parihar | A61B 17/07207 |
| 9,717,497 B2 | 8/2017 | Zerkle et al. | |
| 9,795,379 B2 | 10/2017 | Leimbach et al. | |
| 9,808,248 B2 | 11/2017 | Hoffman | |
| 9,839,421 B2 | 12/2017 | Zerkle et al. | |
| 9,907,554 B2 * | 3/2018 | Morgan | A61B 17/07207 |
| 10,092,292 B2 | 10/2018 | Boudreaux et al. | |
| 10,166,023 B2 | 1/2019 | Vendely et al. | |
| 10,349,939 B2 | 7/2019 | Shelton, IV et al. | |
| 10,426,481 B2 * | 10/2019 | Aronhalt | A61B 17/07292 |
| 10,441,285 B2 | 10/2019 | Shelton, IV et al. | |
| 10,524,788 B2 | 1/2020 | Vendely et al. | |
| 10,568,621 B2 | 2/2020 | Shelton, IV et al. | |
| 10,588,623 B2 | 3/2020 | Schmid et al. | |
| 10,624,861 B2 | 4/2020 | Widenhouse et al. | |
| 10,639,039 B2 | 5/2020 | Vendely et al. | |
| 10,667,808 B2 | 6/2020 | Baxter, III et al. | |
| 10,758,398 B2 * | 9/2020 | Murthy Aravalli | A61B 17/1114 |
| 10,945,731 B2 | 3/2021 | Baxter, III et al. | |
| 10,966,722 B2 | 4/2021 | Shelton, IV et al. | |
| 10,987,107 B2 * | 4/2021 | Sgroi, Jr. | A61B 17/0643 |
| 11,058,425 B2 | 7/2021 | Widenhouse et al. | |
| 11,382,625 B2 | 7/2022 | Huitema et al. | |
| 11,660,093 B2 | 5/2023 | Bakos et al. | |
| 11,857,190 B2 | 1/2024 | Strang et al. | |
| 2002/0165563 A1 | 11/2002 | Grant et al. | |
| 2005/0263562 A1 | 12/2005 | Shelton, IV et al. | |
| 2009/0020584 A1 | 1/2009 | Soltz et al. | |
| 2009/0206143 A1 | 8/2009 | Huitema et al. | |
| 2010/0331880 A1 | 12/2010 | Stopek et al. | |
| 2011/0077629 A1 | 3/2011 | Tanaka et al. | |
| 2012/0080336 A1 | 4/2012 | Shelton, IV et al. | |
| 2012/0080498 A1 | 4/2012 | Shelton, IV et al. | |
| 2012/0080503 A1 | 4/2012 | Woodard, Jr. et al. | |
| 2012/0083836 A1 | 4/2012 | Shelton, IV et al. | |
| 2012/0125792 A1 | 5/2012 | Cassivi | |
| 2012/0136345 A1 | 5/2012 | Takashino | |
| 2012/0241492 A1 | 9/2012 | Shelton, IV et al. | |
| 2012/0241503 A1 | 9/2012 | Baxter, III et al. | |
| 2012/0241505 A1 | 9/2012 | Alexander, III et al. | |
| 2013/0146641 A1 | 6/2013 | Shelton, IV et al. | |
| 2013/0146643 A1 | 6/2013 | Schmid et al. | |
| 2013/0153635 A1 | 6/2013 | Hodgkinson | |
| 2013/0214030 A1 | 8/2013 | Aronhalt et al. | |
| 2013/0221062 A1 | 8/2013 | Hodgkinson | |
| 2013/0256376 A1 | 10/2013 | Barton et al. | |
| 2014/0131419 A1 | 5/2014 | Bettuchi | |
| 2014/0158741 A1 | 6/2014 | Woodard, Jr. et al. | |
| 2014/0166721 A1 | 6/2014 | Stevenson et al. | |
| 2014/0209658 A1 | 7/2014 | Skalla et al. | |
| 2014/0224686 A1 | 8/2014 | Aronhalt et al. | |
| 2014/0291382 A1 | 10/2014 | Lloyd et al. | |
| 2015/0136831 A1 | 5/2015 | Baxter, III et al. | |
| 2015/0196296 A1 | 7/2015 | Swayze et al. | |
| 2015/0196348 A1 | 7/2015 | Yates et al. | |
| 2015/0282809 A1 | 10/2015 | Shelton, IV et al. | |
| 2016/0278764 A1 | 9/2016 | Shelton, IV et al. | |
| 2016/0278765 A1 | 9/2016 | Shelton, IV et al. | |
| 2016/0278774 A1 | 9/2016 | Shelton, IV et al. | |
| 2017/0055981 A1 | 3/2017 | Vendely et al. | |
| 2017/0055986 A1 | 3/2017 | Harris et al. | |
| 2017/0086838 A1 | 3/2017 | Harris et al. | |
| 2017/0086841 A1 | 3/2017 | Vendely et al. | |
| 2017/0086845 A1 | 3/2017 | Vendely et al. | |
| 2017/0119390 A1 | 5/2017 | Schellin et al. | |
| 2017/0119392 A1 | 5/2017 | Shelton, IV et al. | |
| 2018/0103952 A1 | 4/2018 | Aronhalt et al. | |
| 2018/0235624 A1 | 8/2018 | Shelton, IV et al. | |
| 2018/0235626 A1 | 8/2018 | Shelton, IV et al. | |
| 2019/0008518 A1 * | 1/2019 | Sgroi, Jr. | A61B 17/1155 |
| 2019/0200978 A1 | 7/2019 | Shelton, IV et al. | |
| 2019/0269402 A1 | 9/2019 | Murray et al. | |
| 2019/0298338 A1 | 10/2019 | Vendely et al. | |
| 2019/0314016 A1 | 10/2019 | Huitema et al. | |
| 2019/0314018 A1 | 10/2019 | Huitema et al. | |
| 2020/0205825 A1 | 7/2020 | Vendely et al. | |
| 2020/0305963 A1 | 10/2020 | Wagner et al. | |
| 2020/0390944 A1 | 12/2020 | Williams et al. | |
| 2021/0128129 A1 | 5/2021 | George et al. | |
| 2022/0061843 A1 | 3/2022 | Vendely et al. | |
| 2022/0160360 A1 | 5/2022 | Harris et al. | |
| 2022/0313247 A1 | 10/2022 | Shelton, IV et al. | |
| 2023/0301656 A1 | 9/2023 | Seow et al. | |
| 2023/0301657 A1 | 9/2023 | Zeiner et al. | |
| 2023/0301674 A1 | 9/2023 | Rector et al. | |
| 2023/0320742 A1 | 10/2023 | Bakos et al. | |

FOREIGN PATENT DOCUMENTS

| | | | |
|---|---|---|---|
| EP | 3150142 | A2 | 4/2017 |
| EP | 3162384 | A1 | 5/2017 |
| EP | 3363387 | A1 | 8/2018 |
| EP | 3424441 | A2 | 1/2019 |
| EP | 3530213 | A2 | 8/2019 |
| EP | 3791802 | A1 | 3/2021 |
| EP | 3791805 | A1 | 3/2021 |
| EP | 3791806 | A1 | 3/2021 |

OTHER PUBLICATIONS

International Search Report and Written Opinion dated Jul. 31, 2023, for International Application No. PCT/IB2023/052804, 21 pages.
International Search Report and Written Opinion dated Aug. 7, 2023, for International Application No. PCT/IB2023/052805, 21 pages.
International Search Report and Written Opinion dated Aug. 9, 2023, for International Application No. PCT/IB2023/052809, 20 pages.
International Search Report and Written Opinion dated Jun. 20, 2023, for International Application No. PCT/IB2023/052810, 16 pages.

* cited by examiner

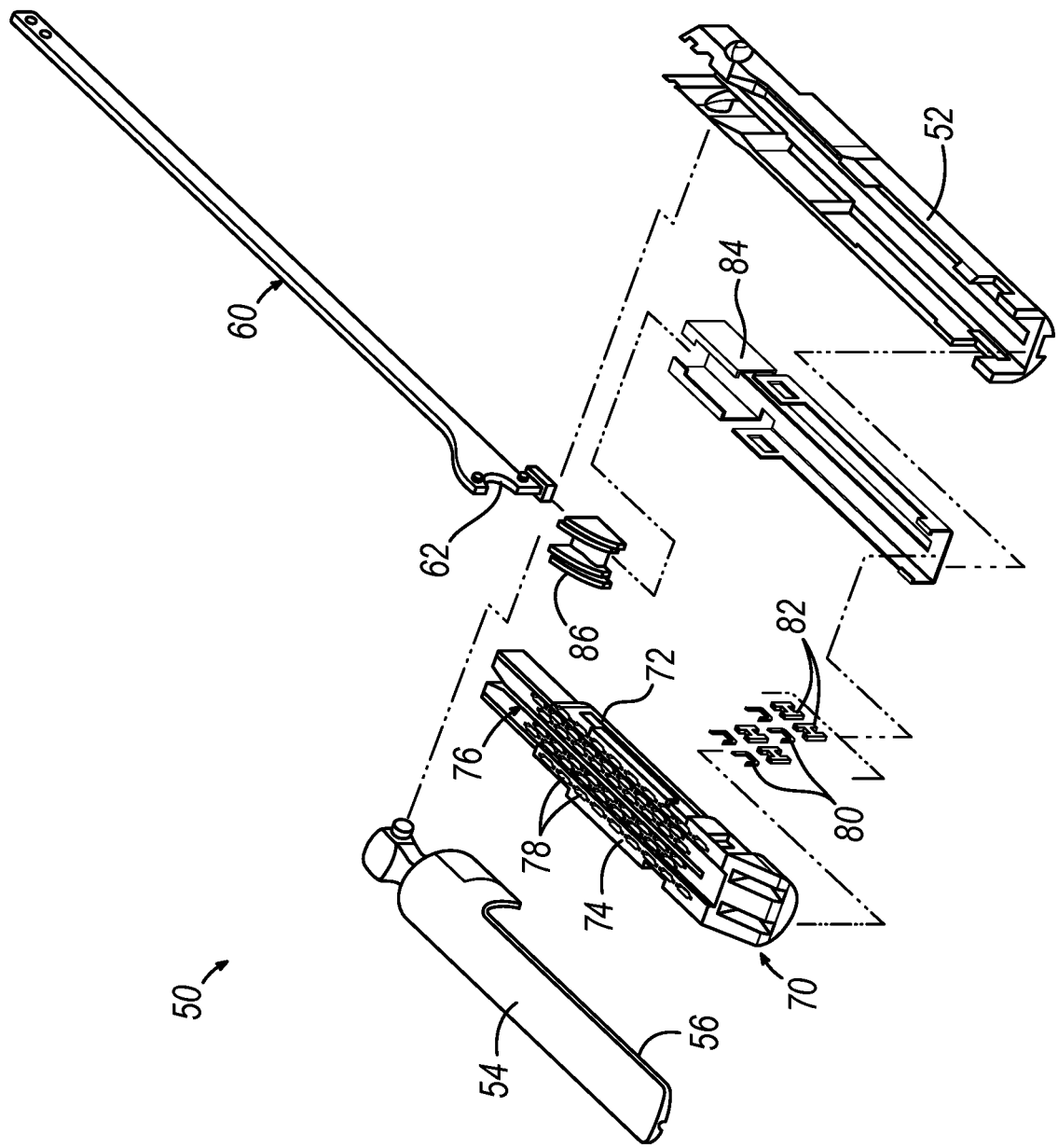

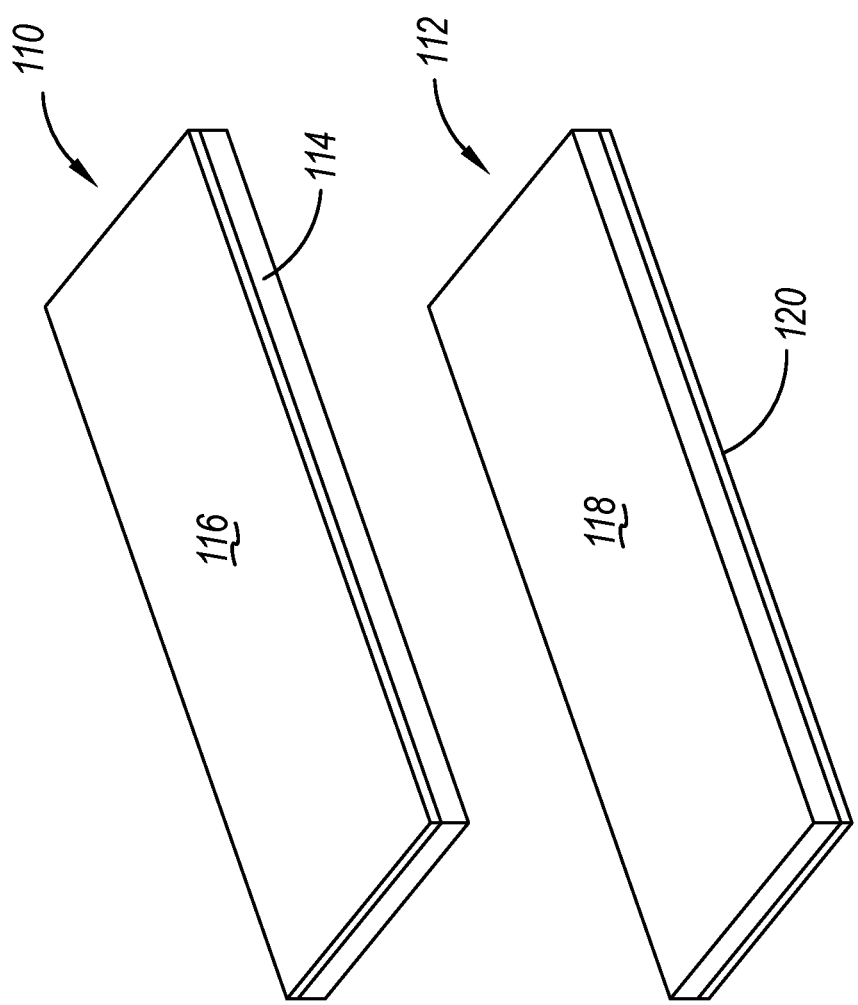

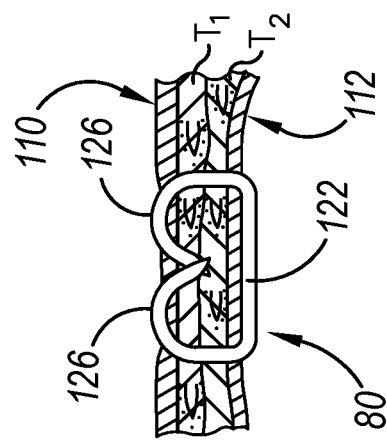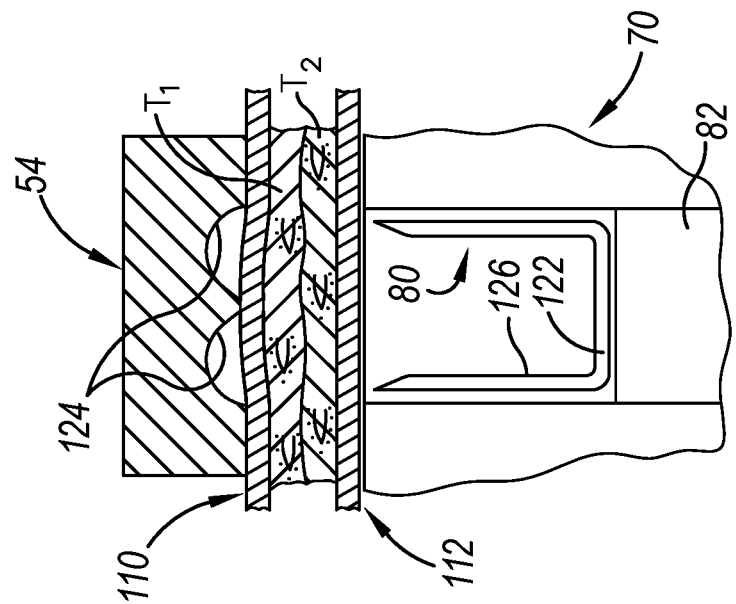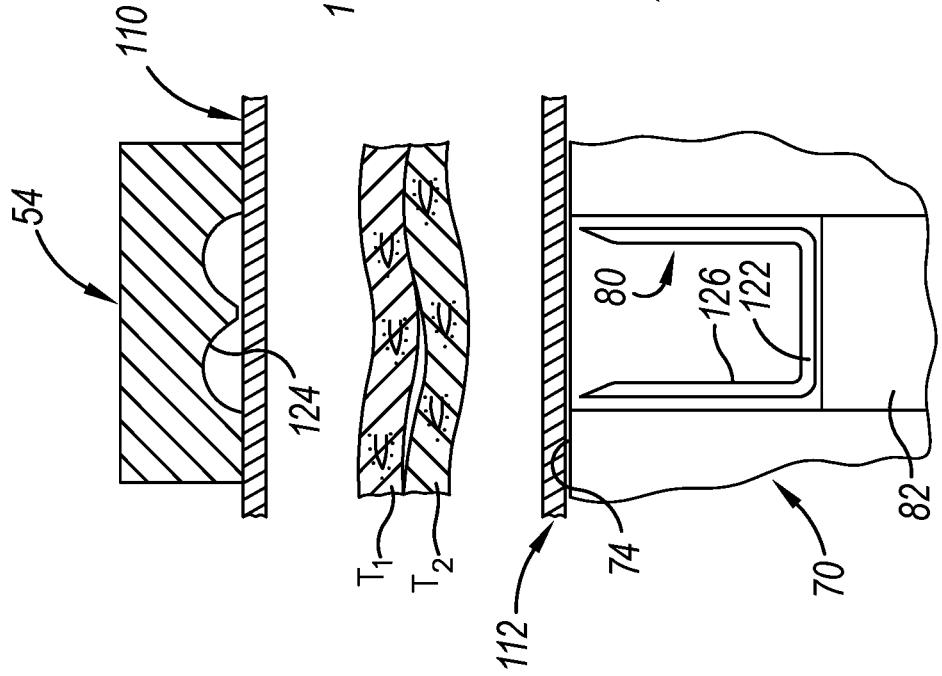

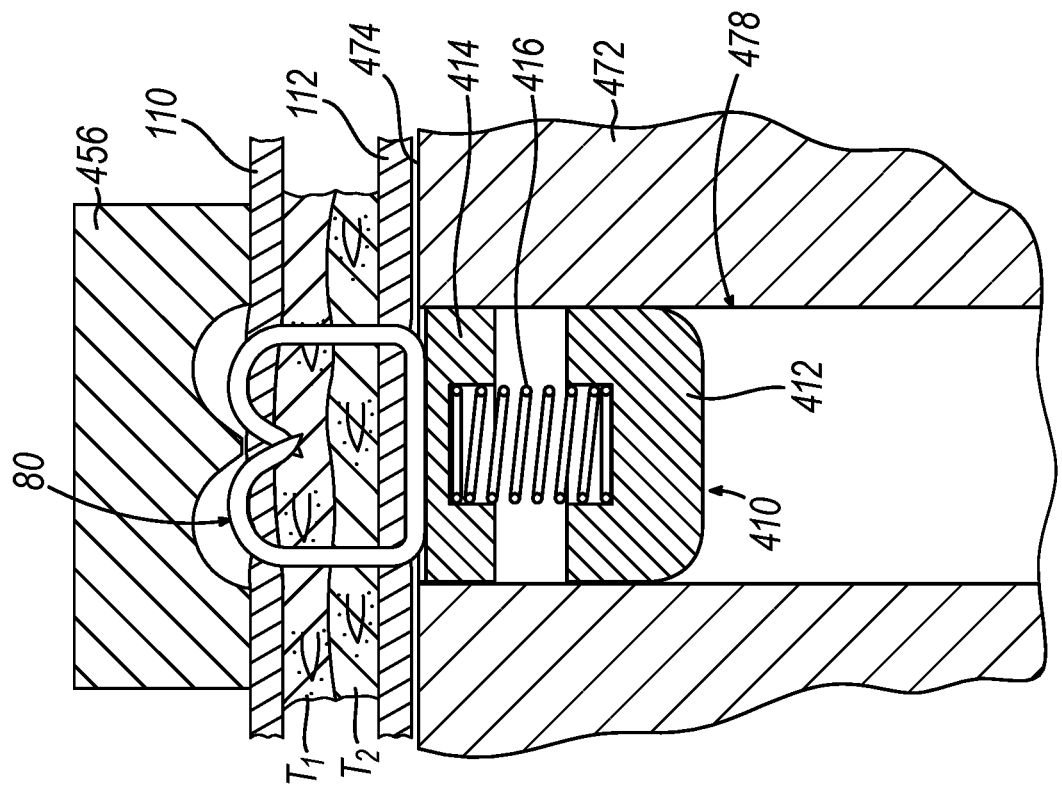
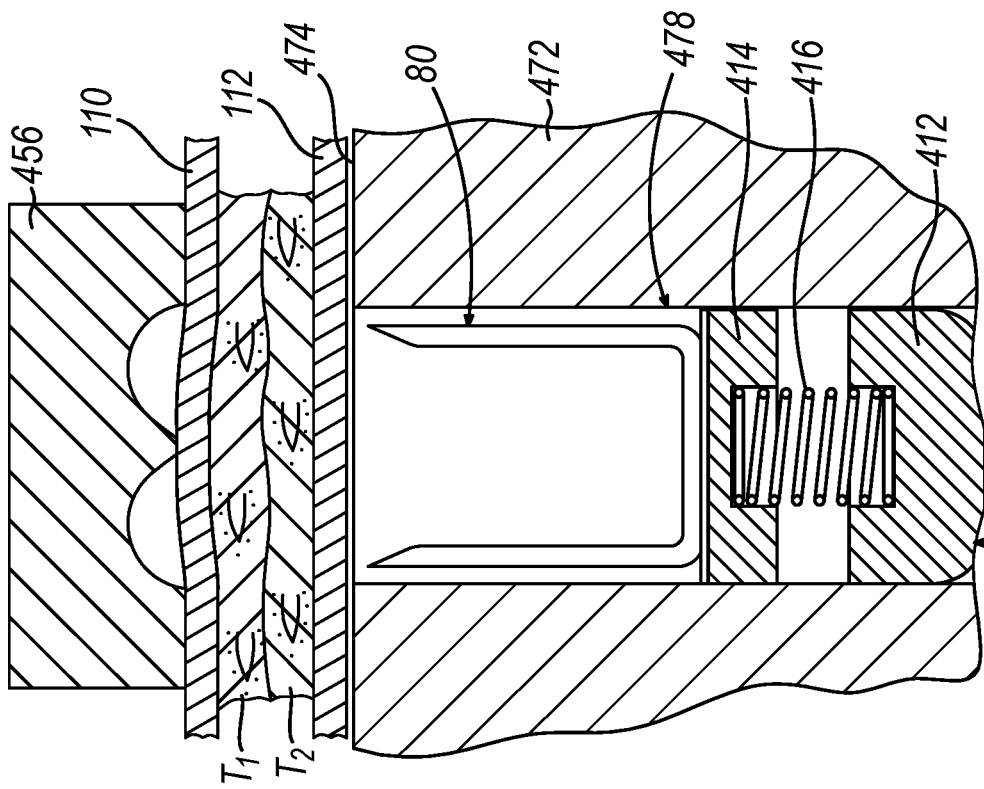
FIG. 22A
FIG. 22B

SURGICAL STAPLER FEATURES FOR STAPLING VARIABLE THICKNESS TISSUE

BACKGROUND

In some surgical settings, endoscopic surgical instruments may be preferred over traditional open surgical devices in order to make use of a smaller incision in the patient, which may reduce post-operative recovery time and complications. Some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,380,696, entitled "Articulating Surgical Stapling Instrument Incorporating a Two-Piece E-Beam Firing Mechanism," issued Jun. 3, 2008; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents and U.S. Patent Publications is incorporated by reference herein.

Surgical staplers may also be used in open procedures and/or other non-endoscopic procedures. By way of example only, a surgical stapler may be inserted through a thoracotomy and thereby between a patient's ribs to reach one or more organs in a thoracic surgical procedure that does not use a trocar as a conduit for the stapler. For instance, the vessels leading to an organ may be severed and closed by a stapler before removal of the organ from the thoracic cavity. Of course, surgical staplers may be used in various other settings and procedures.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 depicts an exploded perspective view of the end effector of FIG. 3;

FIG. 7 depicts a perspective view of an exemplary pair of adjuncts in the form of buttress assemblies, each of which may be applied to a jaw of the end effector of FIG. 3;

FIG. 8A depicts a cross-sectional end view of a portion of the end effector of FIG. 3 with the buttress assemblies of FIG. 7 applied to the upper and lower jaws of the end effector, showing the end effector jaws in an open state with tissue positioned between the upper and lower jaws;

FIG. 8B depicts a cross-sectional end view of the end effector and buttress assemblies of FIG. 8A, showing the end effector jaws in a closed state on the tissue;

FIG. 8C depicts a cross-sectional view of a formed staple and the buttress assemblies of FIG. 8A after having been secured to the tissue by the end effector of FIG. 3;

FIG. 22A depicts a cross-sectional end view of a portion of the end effector of FIG. 17A with the buttress assemblies of FIG. 7 applied to the upper and lower jaws of the end effector, showing the end effector jaws in a closed state with tissue having a first thickness positioned between the upper and lower jaws;

FIG. 22B depicts a cross-sectional view of a formed staple and the buttress assemblies of FIG. 22A after having been secured to the tissue having a first thickness by the end effector of FIG. 17A;

Figure 1:
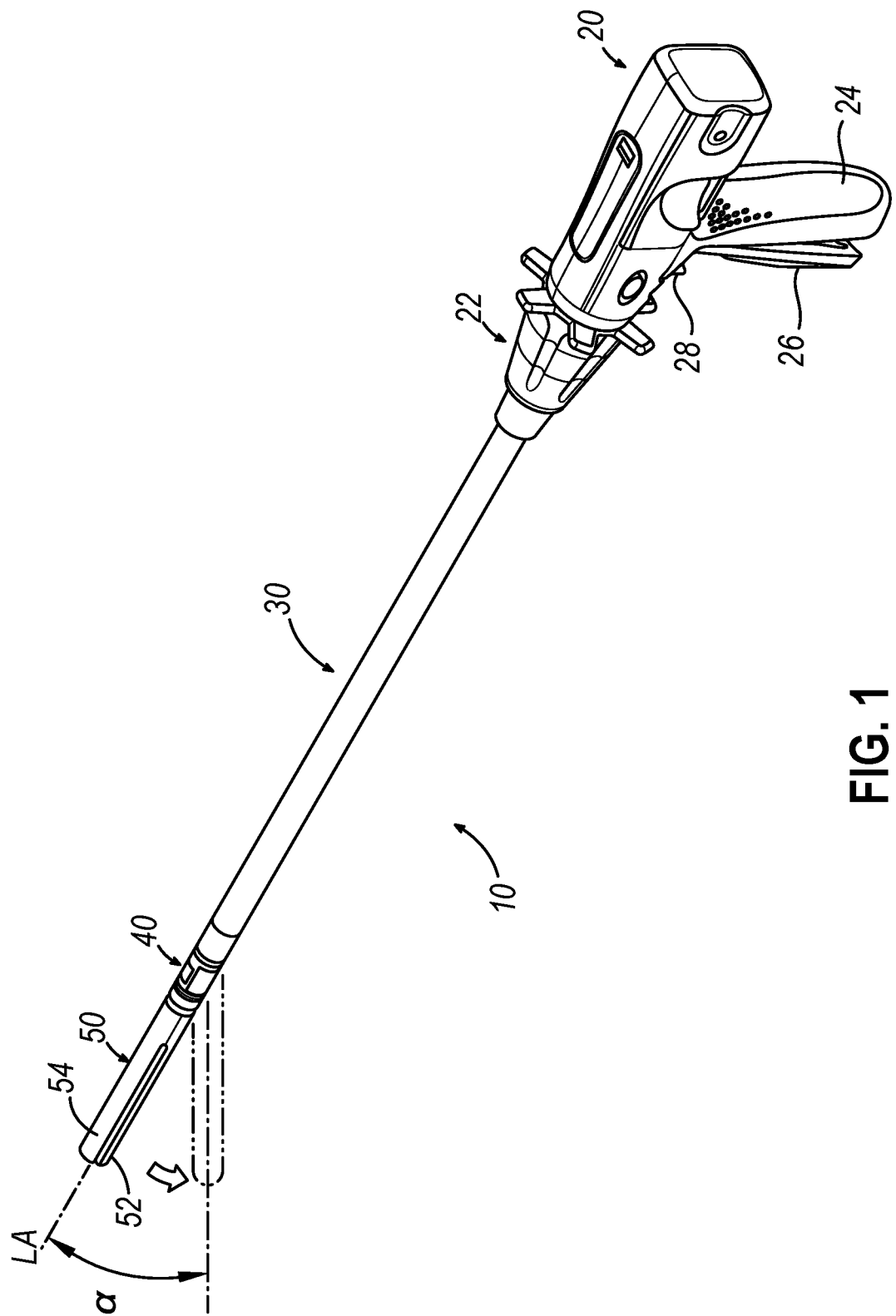
FIG. 1 depicts a perspective view of an exemplary surgical stapler.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "lateral," "transverse," "bottom," "top," are relative terms to provide additional clarity to the figure descriptions provided below. The terms "upper," "lower," "lateral," "transverse," "bottom," "top," are thus not intended to unnecessarily limit the invention described herein.

I. Exemplary Surgical Stapler

Figure 2:
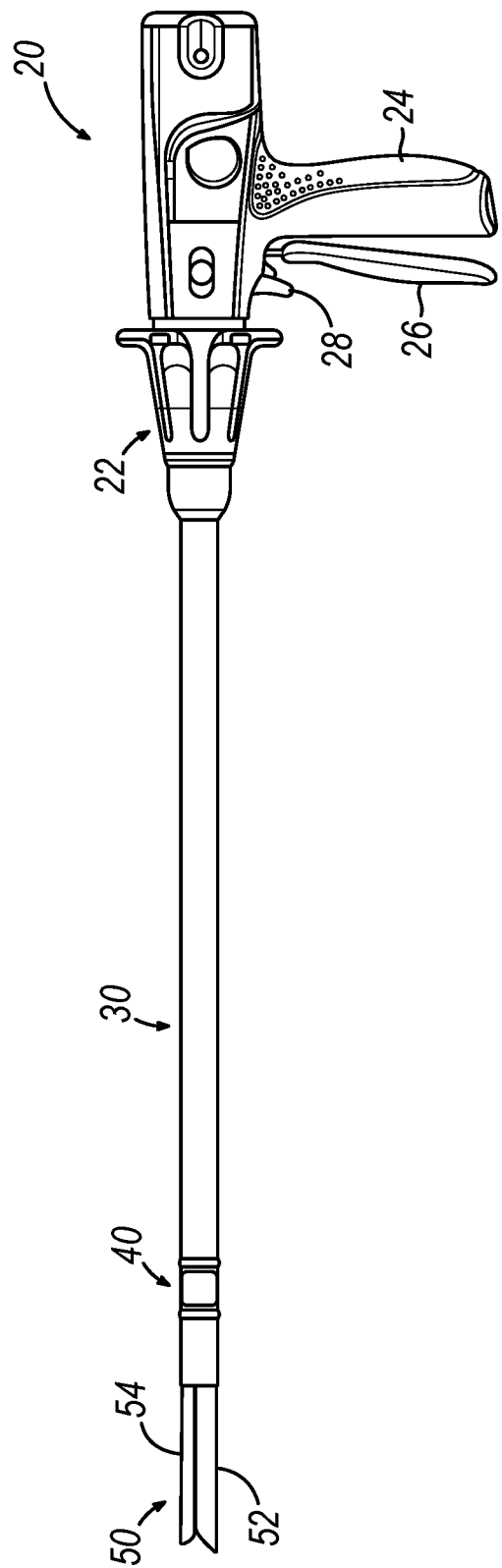
FIG. 2 depicts a side elevational view of the surgical stapler of FIG. 1.

FIGS. 1-6 show an exemplary surgical stapler (10) that is sized for insertion through a trocar cannula or an incision (e.g., thoracotomy, etc.) to a surgical site in a patient for performing a surgical procedure. As shown in FIGS. 1 and 2, surgical stapler (10) of the present example includes a proximal body in the form of a handle assembly (20), a shaft assembly (30) extending distally from handle assembly (20) and terminating at an articulation joint (40), and an end effector (50) coupled with the distal end of shaft assembly (30) via articulation joint (40). Articulation joint (40) is configured to enable lateral deflection, either actively or passively, of end effector (50) relative to a longitudinal axis (LA) of shaft assembly (30) to a desired angle (a) via actuation of an articulation control feature (22) of handle assembly (20).

Figure 3:
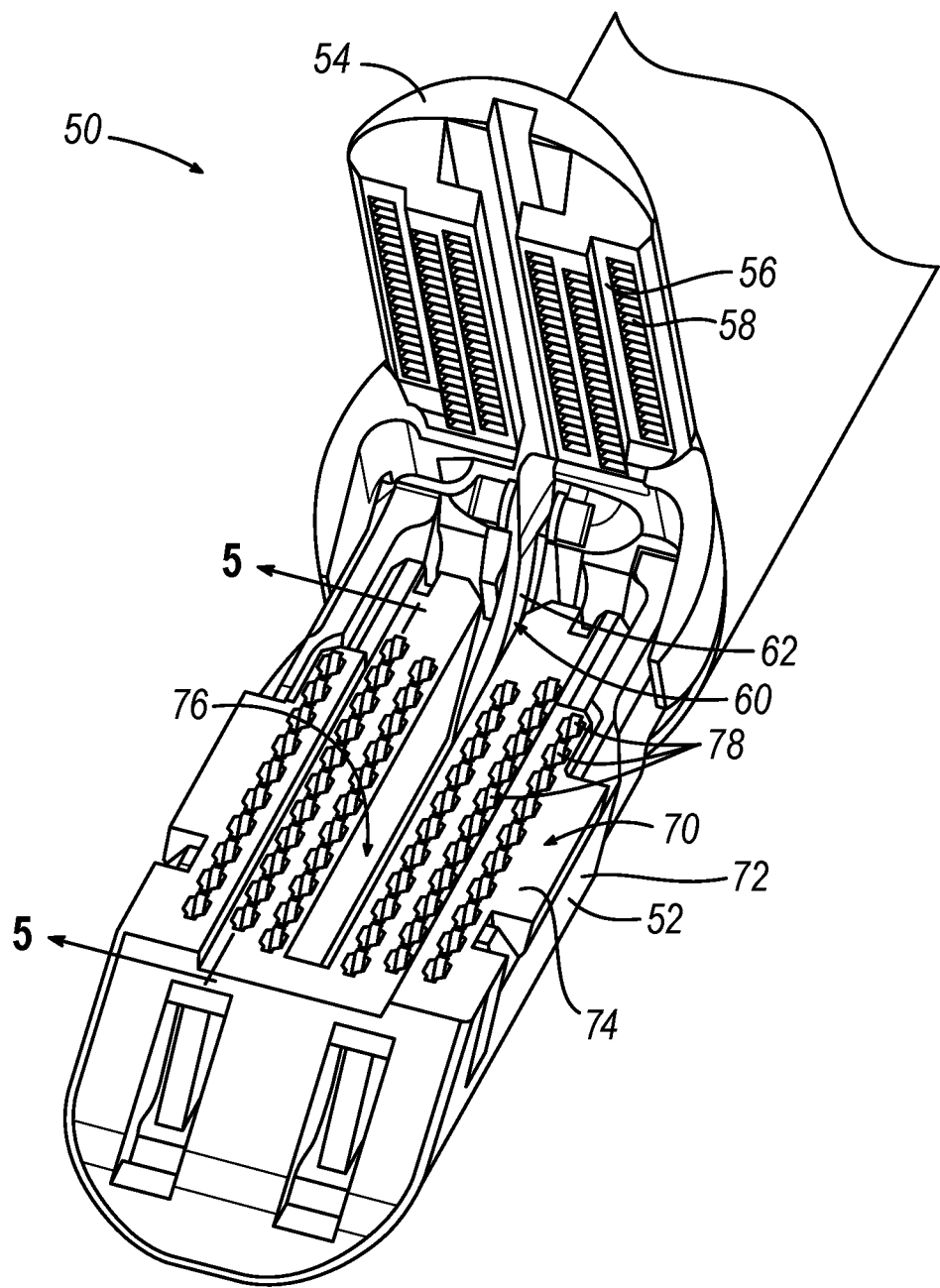
FIG. 3 depicts a perspective view of an end effector of the surgical stapler of FIG. 1 in an open state.

As shown best in FIGS. 3 and 4, end effector (50) includes a lower jaw (52) that supports a stapling assembly in the form of a replaceable staple cartridge (70), and an upper jaw (54) that presents an anvil (56) having a plurality of staple forming pockets (58). Upper jaw (54) is configured to pivot relative to lower jaw (52) to clamp tissue between staple cartridge (70) and anvil (56) and subsequently form staples deployed by staple cartridge (70). End effector (50) further includes an elongate firing member (60) configured to translate distally through end effector (50) to drive staples from staple cartridge (70) toward anvil (56) and simultaneously cut tissue with a distally presented cutting edge (62). Accordingly, end effector (50) is operable to clamp, staple, and cut tissue.

As shown best in FIGS. 1 and 2, handle assembly (20) further includes a pistol grip (24), a closure trigger (26), and a firing trigger (28). Closure trigger (26) is pivotable toward pistol grip (24) to pivotably actuate upper jaw (54) toward lower jaw (52) and thereby close end effector (50) on tissue. Firing trigger (28) is then pivotable toward pistol grip (24) to fire end effector (50) on the clamped tissue. More specifically, actuation of firing trigger (28) causes firing member (60) to translate distally through end effector (50), including staple cartridge (70), to thereby staple and simultaneously cut the clamped tissue.

As shown in FIGS. 3-5B, staple cartridge (70) includes a cartridge body (72) having an upwardly facing deck (74), an elongate slot (76) extending along a central axis of cartridge body (72) and opening upwardly through deck (74), and a plurality of staple openings (78) (also known as apertures) extending through deck (74) on each side of elongate slot (76). Each staple opening (78) slidably houses an unformed staple (80) and a respective staple driver (82) positioned beneath staple (80). A lower tray (84), also known as a pan, encloses an underside of cartridge body (72) and thereby retains staples (80) and staple drivers (82) within cartridge body (72). A wedge sled (86) is slidably disposed within cartridge body (72) and includes upwardly presented cam surfaces configured to engage the undersides of staple drivers (82).

Figure 5A:
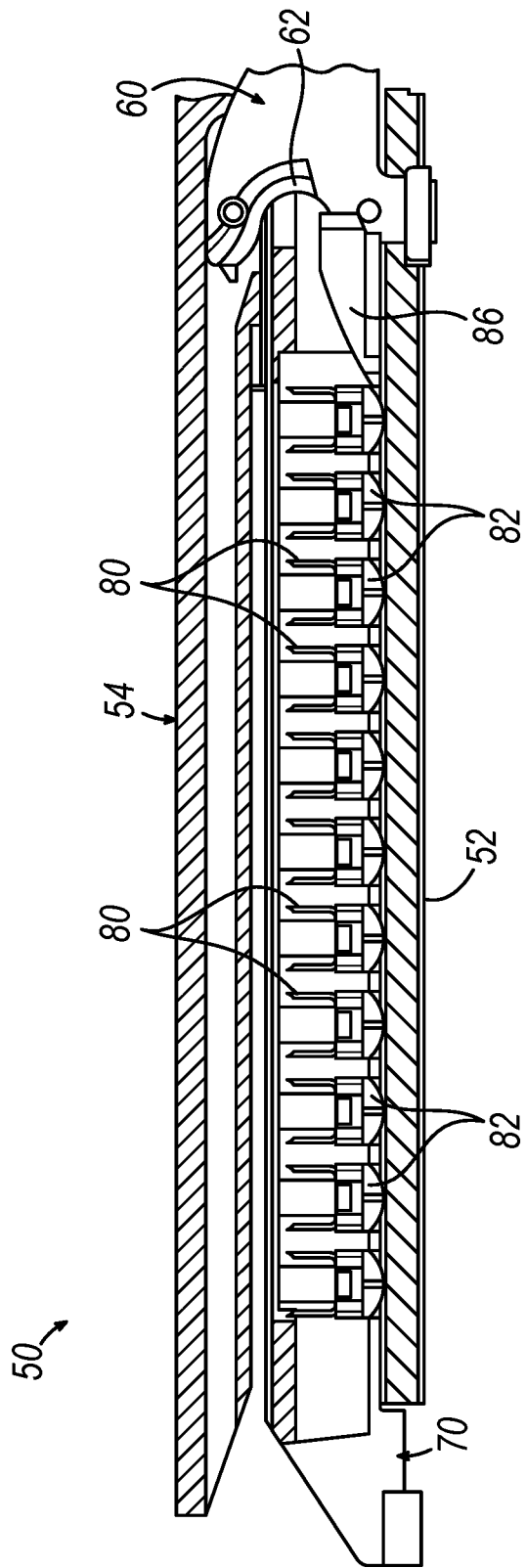
FIG. 5A depicts a side cross-sectional view of the end effector of FIG. 3, taken along line 5-5 of FIG. 3, with a firing member in a proximal position.
Figure 5B:
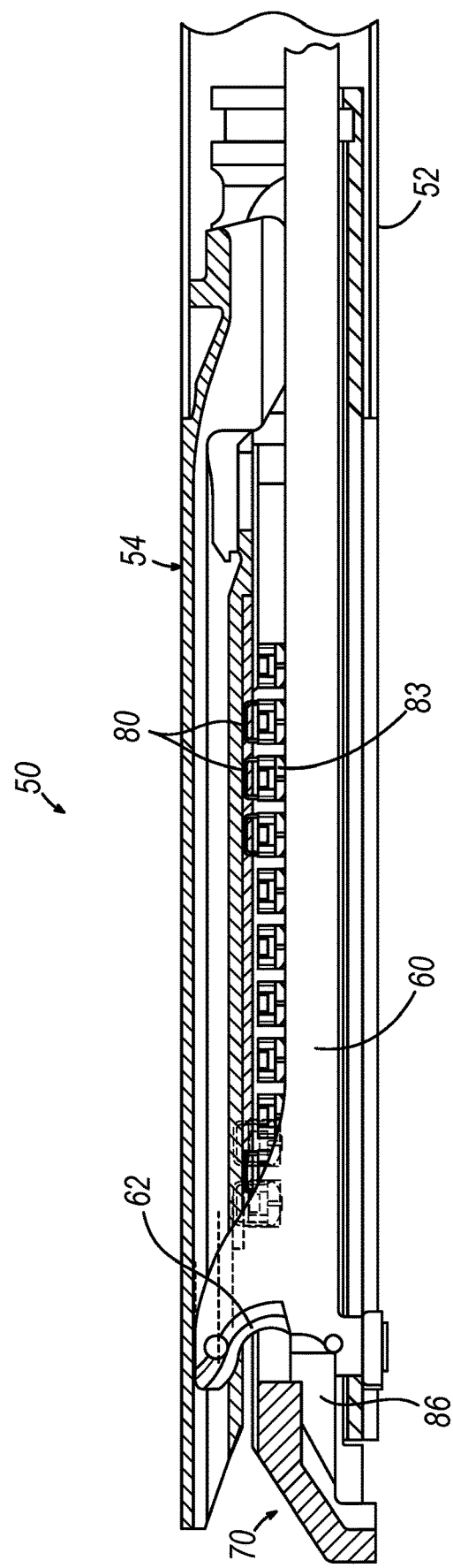
FIG. 5B depicts a side cross-sectional view of the end effector of FIG. 3, taken along line 5-5 of FIG. 3, with the firing member in a distal position.

FIGS. 5A-5B show a firing stroke of surgical stapler (10) during which firing member (60) is actuated distally through end effector (50), including elongate slot (76) of staple cartridge (70). A distal end of firing member (60) drives wedge sled (86) distally to cam staple drivers (82) upwardly and thereby drive the respective staples (80) outwardly from staple openings (78). The legs of staples (80) pass through clamped tissue (not shown) and are then formed by staple forming pockets (58) of anvil (56) (see FIG. 3). Simultaneously, the clamped tissue is severed by cutting edge (62) of firing member (60).

Figure 6:
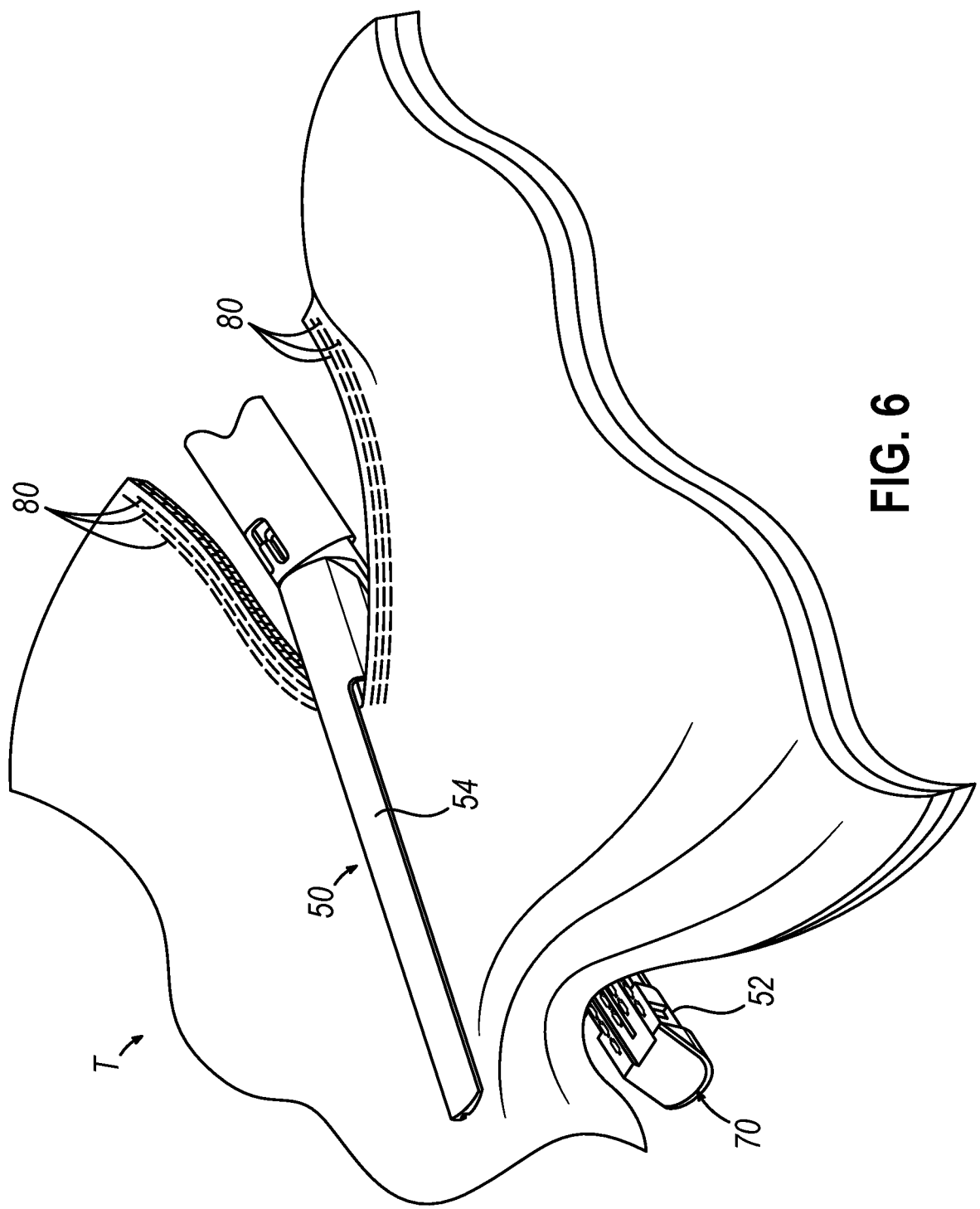
FIG. 6 depicts a perspective view of the end effector of FIG. 3, positioned at tissue and having been fired once in the tissue.

FIG. 6 shows end effector (50) after having been actuated through a single firing stroke through tissue (T). Cutting edge (62) of firing member (60) has cut through tissue (T), and staple drivers (82) have driven three alternating rows of staples (80) through tissue (T) on each side of the cut line produced by cutting edge (62). After the first firing stroke is completed, end effector (50) is withdrawn from the patient, spent staple cartridge (70) is replaced with a new staple cartridge (70), and end effector (50) is then again inserted into the patient to reach the stapling site for further cutting and stapling. This process may be repeated until the desired quantity and pattern of firing strokes across the tissue (T) has been completed.

Surgical stapler (10) may be further constructed and operable in accordance with any of the teachings of the following references, the disclosures of which are incorporated by reference herein: U.S. Pat. No. 8,210,411, entitled "Motor-Driven Surgical Instrument," issued Jul. 3, 2012; U.S. Pat. No. 9,186,142, entitled "Surgical Instrument End Effector Articulation Drive with Pinion and Opposing Racks," issued on Nov. 17, 2015; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; U.S. Pat. No. 9,717,497, entitled "Lockout Feature for Movable Cutting Member of Surgical Instrument," issued Aug. 1, 2017; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 9,839,421, entitled "Jaw Closure Feature for End Effector of Surgical Instrument," issued Dec. 12, 2017; and/or U.S. Pat. No. 10,092,292, entitled "Staple Forming Features for Surgical Stapling Instrument," issued Oct. 9, 2018.

II. Exemplary Buttress Assembly

In some instances, it may be desirable to equip end effector (50) of surgical stapler (10) with an adjunct, also known as a buttress or a tissue thickness compensator, to reinforce the mechanical fastening of tissue provided by staples (80). Such a buttress may prevent the applied staples (80) from pulling through the tissue and may otherwise reduce a risk of tissue tearing at or near the site of applied staples (80). In addition to or as an alternative to providing structural support and integrity to a line of staples (80), a buttress may provide various other kinds of effects such as spacing or gap-filling, administration of therapeutic agents, and/or other effects. In some instances, a buttress may be provided on upper deck (74) of staple cartridge (70). In some other instances, a buttress may be provided on the surface of anvil (56) that faces staple cartridge (70). It should also be understood that a first buttress may be provided on upper deck (74) of staple cartridge (70) while a second buttress is provided on anvil (56) of the same end effector (50).

A. Exemplary Composition of Buttress Assembly

FIG. 7 shows an exemplary pair of adjuncts in the form of buttress assemblies (110, 112) (each also referred to individually as a "buttress"). Buttress assembly (110) of this example comprises a buttress body (114) and an upper adhesive layer (116). Similarly, buttress assembly (112) comprises a buttress body (118) and a lower adhesive layer (120). In the present example, each buttress body (114, 118) comprises a strong yet flexible material configured to structurally support a line of staples (80). By way of example only, each buttress body (114, 118) may comprise a mesh of polyglactin 910 material by Ethicon, Inc. of Somerville, New Jersey. Alternatively, any other suitable materials or combinations of materials may be used in addition to or as an alternative to polyglactin 910 material to form each buttress body (114, 118).

Each buttress body (114, 118) may comprise a material including, for example, a hemostatic agent such as fibrin to assist in coagulating blood and reduce bleeding at the severed and/or stapled surgical site along tissue ($T_1$, $T_2$). As another merely illustrative example, each buttress body (114, 118) may comprise other adjuncts or hemostatic agents such as thrombin may be used such that each buttress body (114, 118) may assist to coagulate blood and reduce the amount of bleeding at the surgical site. Other adjuncts or reagents that may be incorporated into each buttress body (114, 118) may further include but are not limited to medical fluid or matrix components.

In the present example, adhesive layer (116) is provided on buttress body (114) to adhere buttress body (114) to an underside (124) of anvil (56). Similarly, adhesive layer (120) is provided on buttress body (118) to adhere buttress body (118) to upper deck (74) of staple cartridge (70). Such an adhesive material may provide proper positioning of buttress body (114, 118) before and during actuation of end effector (50); then allow buttress body (114, 118) to separate from end effector (50) after end effector (50) has been actuated, without causing damage to buttress body (114, 118) that is substantial enough to compromise the proper subsequent functioning of buttress body (114, 118).

B. Exemplary Stapling of Tissue with Buttress Assemblies

FIGS. 8A-8C show an exemplary sequence in which surgical stapler end effector (50), which has been loaded with buttress assemblies (110, 112), is actuated to drive staples (80) through two opposed layers of tissue ($T_1$, $T_2$), with buttress assemblies (110, 112) being secured to the same layers of tissue ($T_1$, $T_2$) by staples (80). In particular, FIG. 8A shows layers of tissue ($T_1$, $T_2$) positioned between anvil (56) and staple cartridge (70), with anvil (56) in the open position. Buttress assembly (110) is adhered to underside (124) of anvil (56) via adhesive layer (116); while buttress assembly (112) is adhered to upper deck (74) of staple cartridge (70) via adhesive layer (120). Layers of tissue ($T_1$, $T_2$) are thus interposed between buttress assemblies (110, 112). Next, anvil (56) is closed against staple cartridge (70) such that layers of tissue ($T_1$, $T_2$) are compressed between anvil (56) and staple cartridge (70), with buttress assemblies (110, 112) engaging opposite surfaces of tissue layers ($T_1$, $T_2$). End effector (50) is then fired as described above, driving staple (80) through buttress assemblies (110, 112) and tissue ($T_1$, $T_2$). As shown in FIG. 8C, a crown (122) of driven staple (80) captures and retains buttress assembly (112) against layer of tissue ($T_2$). Deformed legs (126) of staple (80) capture and retain buttress assembly (110) against layer of tissue ($T_1$).

Figure 9:
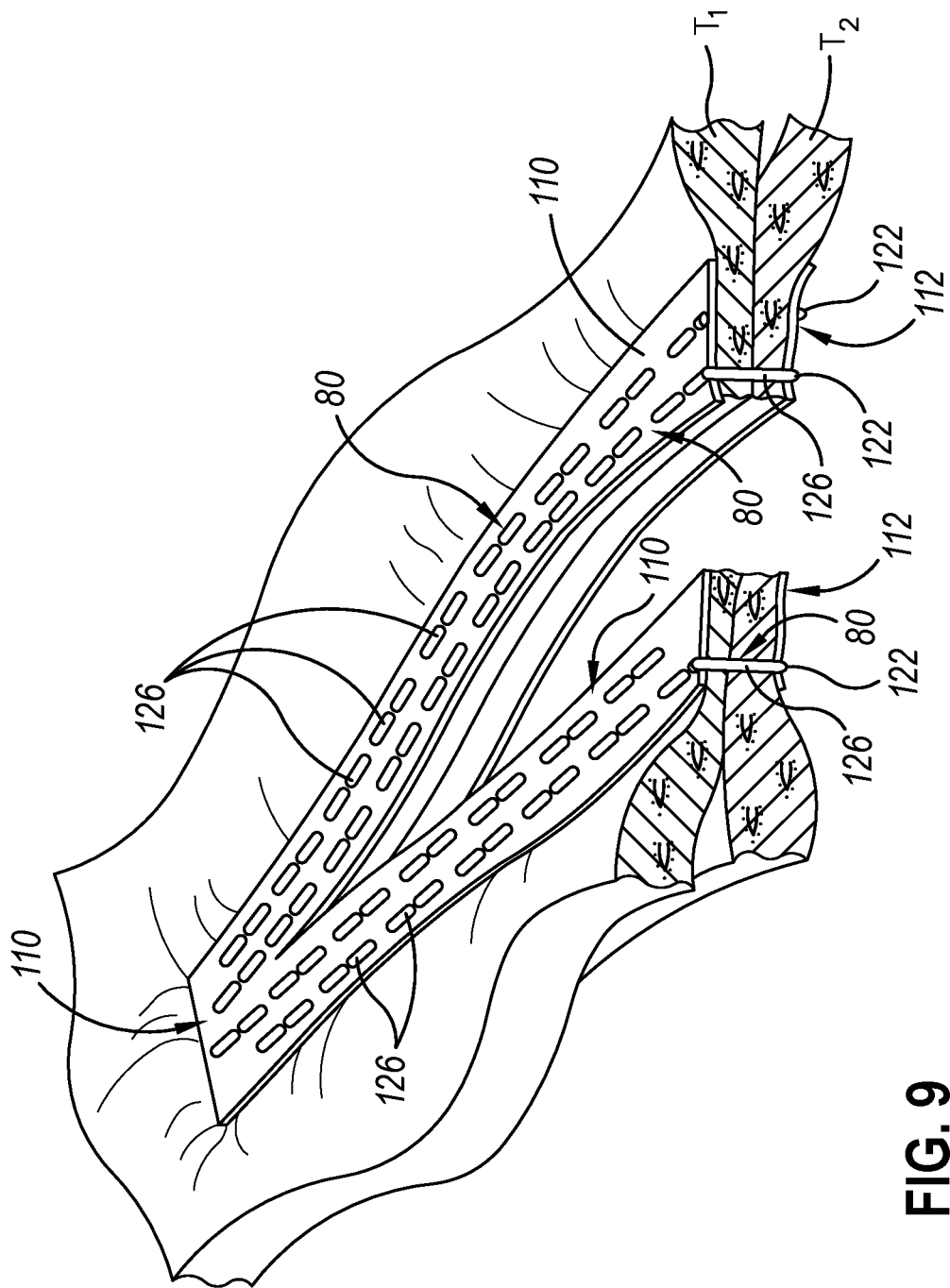
FIG. 9 depicts a perspective view of formed staples and the buttress assemblies of FIG. 8A after having been secured to the tissue by the end effector of FIG. 3.
Figure 10:
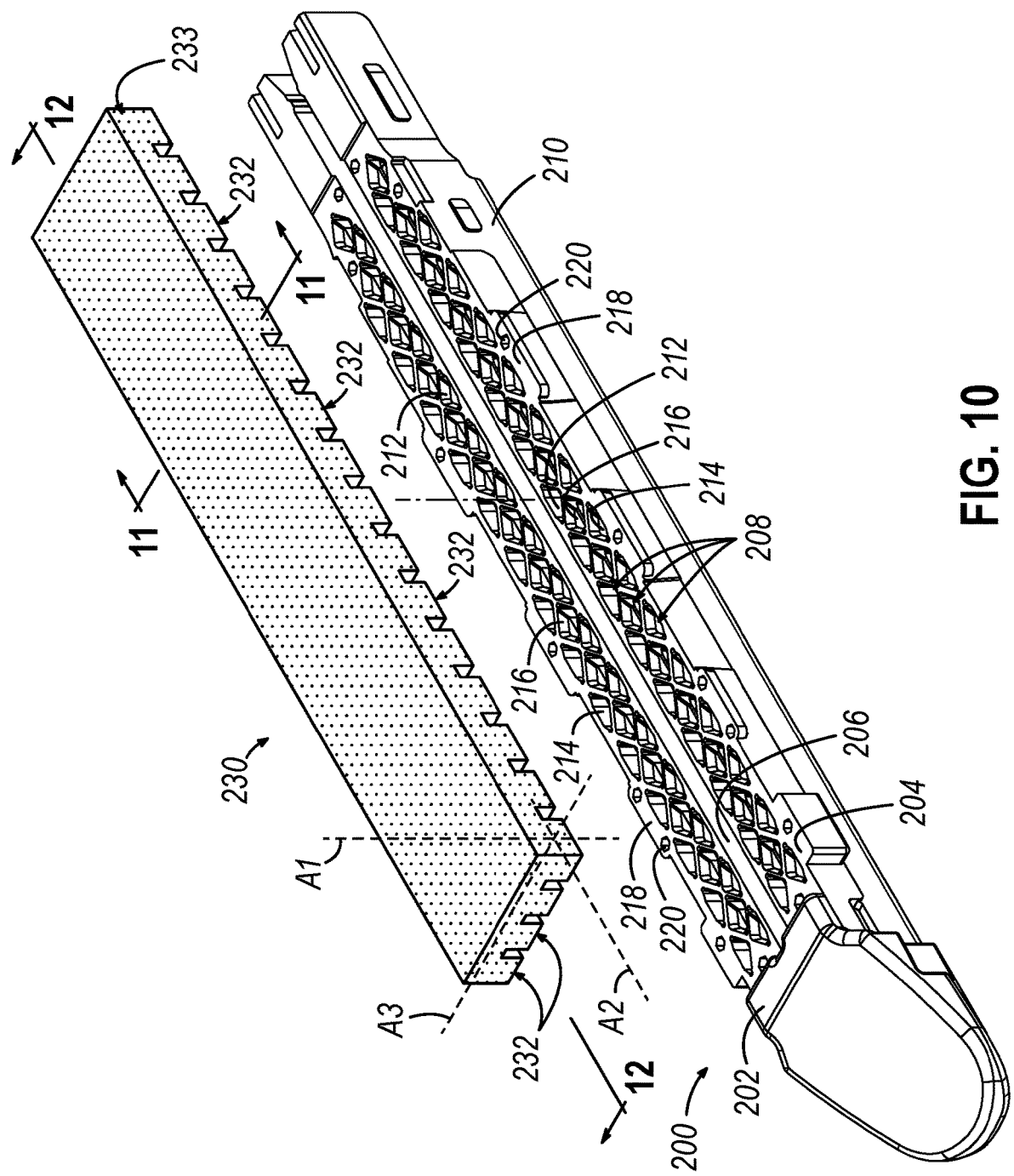
FIG. 10 depicts a perspective view of another exemplary staple cartridge in combination with a first alternative exemplary adjunct.

A series of staples (80) similarly capture and retain buttress assemblies (110, 112) against layers of tissue ($T_1$, $T_2$), thereby securing buttress assemblies (110, 112) to tissue ($T_1$, $T_2$) as shown in FIG. 10. As end effector (50) is pulled away from tissue ($T_1$, $T_2$) after deploying staples (80) and buttress assemblies (110, 112), buttress assemblies (110, 112) disengage end effector such that buttress assemblies (110, 112) remain secured to tissue ($T_1$, $T_2$) with staples (80). Buttress assemblies (110, 112) thus provide structural reinforcement to the lines of staples (80) formed in tissue ($T_1$, $T_2$). As can also be seen in FIG. 9, distally presented cutting edge (62) of firing member (60) also cuts through a centerline of buttress assemblies (110, 112), separating each buttress assembly (110, 112) into a corresponding pair of sections, such that each section remains secured to a respective severed region of tissue ($T_1$, $T_2$).

During use, surgical instrument (10) may be actuated multiple times during a single surgical procedure such that it may be desirable to enable an operator to repeatedly and easily load buttress assemblies (110, 112) onto lower jaw and anvil (52, 54) during that single surgical procedure. Accordingly, it may be desirable to use an adjunct applicator, also referred to as a buttress applier cartridge, to apply buttress assemblies (110, 112) to lower jaw and anvil (52, 54). Exemplary versions of such an applicator are disclosed in U.S. patent application Ser. No. 17/022,520, entitled "Method of Applying Buttress to End Effector of Surgical Stapler," filed Sep. 16, 2020, issued as U.S. Pat. No. 11,660,093 on May 30, 2023, the disclosure of which is incorporated by reference herein.

It will be appreciated that exemplary adjuncts and adjunct applicators may be further configured in accordance with one or more teachings of U.S. Pat. No. 10,166,023, entitled "Method of Applying a Buttress to a Surgical Stapler End Effector," issued Jan. 1, 2019; U.S. Pat. No. 10,349,939, entitled "Method of Applying a Buttress to a Surgical Stapler," issued Jul. 16, 2019; and U.S. Pat. Pub. No. 2012/0080336, entitled "Staple Cartridge Comprising Staples Positioned Within a Compressible Portion Thereof," published Apr. 5, 2012, now abandoned, the disclosures of which are incorporated by reference herein.

III. Exemplary Compressible Adjunct

Figure 11:
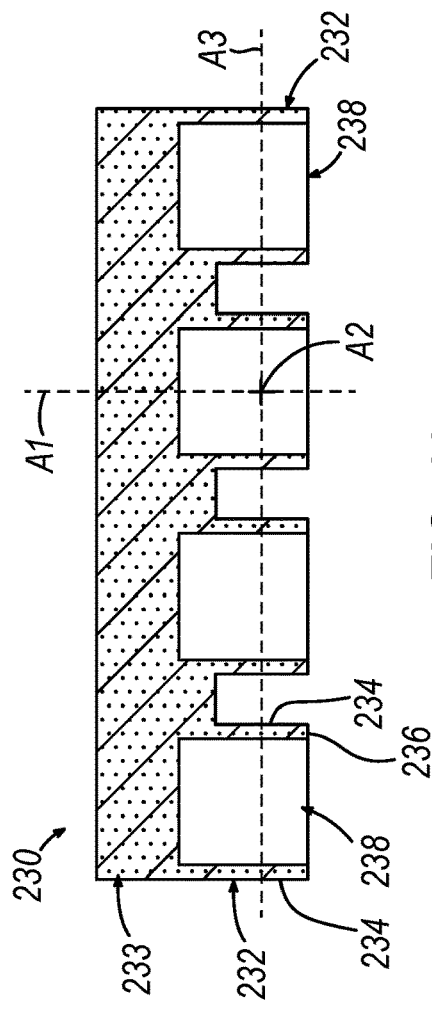
FIG. 11 depicts a cross-sectional view of the adjunct of FIG. 10, taken along line 11-11 of FIG. 10.
Figure 12:
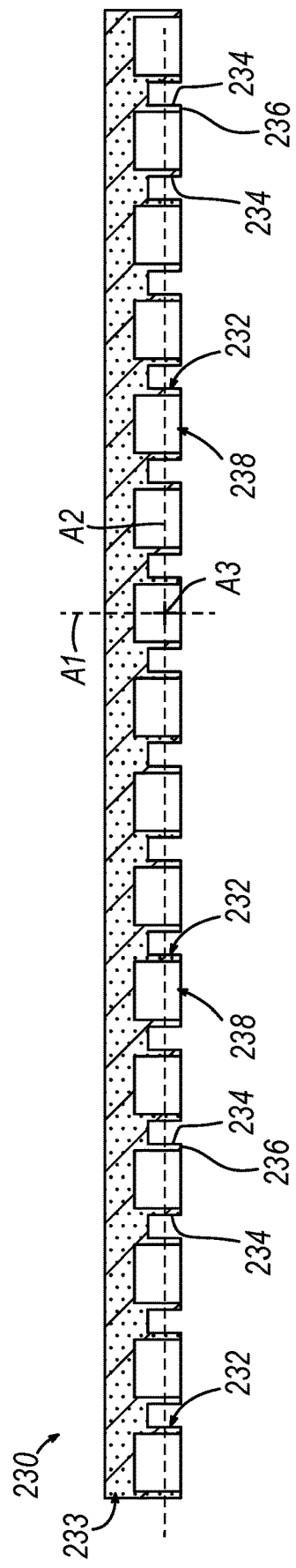
FIG. 12 depicts a cross-sectional view of the adjunct of FIG. 10, taken along line 12-12 of FIG. 10.

In some instances, it may be desirable to employ an adjunct having an enhanced degree of compressibility in a direction orthogonal to the stapling surfaces of end effector (50). Such an adjunct may be configured to apply a compression spring force to stapled tissue consistently along the entire length of the formed staple pattern, thereby ensuring a secure seal of tissue having a thickness that varies along a length of the formed staple pattern and end effector (50). FIGS. 10-12 show an example of such an adjunct (230), also referred to herein as a buttress or cushion, in combination with a staple cartridge (200). Staple cartridge (200) and adjunct (230) are configured for use with end effector (50) and are similar to staple cartridge (70) and buttress assembly (110, 112) described above except as otherwise described below.

It will be appreciated that staple cartridge (200) and/or adjunct (230) may be further configured in accordance with teachings of any one of more the following references, the disclosures of which are incorporated by reference herein: U.S. Pat. No. 10,441,285, entitled "Tissue Thickness Compensator Comprising Tissue Ingrowth Features," issued Oct. 15, 2019; U.S. Pat. No. 10,524,788, entitled "Compressible Adjunct with Attachment Regions," issued Jan. 7, 2020; U.S. Pat. No. 10,568,621, entitled "Surgical Staple Buttress with Integral Adhesive for Releasably Attaching to a Surgical Stapler," issued Feb. 25, 2020; U.S. Pat. No. 10,588,623, entitled "Adhesive Film Laminate," issued Mar. 17, 2020; U.S. Pat. No. 10,624,861, entitled "Tissue Thickness Compensator Configured to Redistribute Compressive Forces," issued Apr. 21, 2020; U.S. Pat. No. 10,667,808, entitled "Staple Cartridge Comprising an Absorbable Adjunct," issued Jun. 2, 2020; U.S. Pat. No. 10,945,731, entitled "Tissue Thickness Compensator Comprising Controlled Release and Expansion," issued Mar. 16, 2021; U.S. Pat. No. 10,966,722, entitled "Adjunct Materials and Methods of Using Same in Surgical Methods for Tissue Sealing," issued Apr. 6, 2021; U.S. Pat. No. 11,058,425, entitled "Implantable Layers for a Surgical Instrument," issued Jul. 13, 2021; and U.S. Pat. Pub. No. 2019/0200978, entitled "Tissue Ingrowth Materials and Method of Using the Same," published Jul. 4, 2019, issued as U.S. Pat. No. 11,219,451 on Jan. 11, 2022.

As shown in FIG. 10, staple cartridge (200) includes a cartridge body (202) having an upwardly facing deck (204), an elongate slot (206) extending along a central axis of cartridge body (202) and opening upwardly through deck (204), and a plurality of staple openings (208) extending through deck (204) on each side of elongate slot (206). Each staple opening (208) slidably houses an unformed staple (not shown), similar to staple (80), and a respective staple driver (not shown), similar to staple driver (82), configured to drive the staple outwardly toward anvil (56) to be formed. A lower tray (210) of staple cartridge (200) retains the staples and staple drivers within cartridge body (202).

Cartridge body (202) of the present example further includes a plurality of upwardly-opening recesses (212, 214, 216) formed in deck (204) and having base surfaces through which staple openings (208) extend. More specifically, on each side of elongate slot (206), deck (204) includes an inner row of triangular recesses (212) each having a medial apex that points transversely away from elongate slot (206); an outer row of triangular recesses (214) each having a medial apex that points transversely toward elongate slot (206); and a middle row of diamond-shaped recesses (216) each having an inner medial apex that points transversely toward elongate slot (206) and an opposed outer medial apex that points transversely away from elongate slot (206). Recesses (212, 214, 216) may cooperate to more securely grip and thereby stabilize clamped tissue during stapling and cutting of the clamped tissue.

Cartridge body (202) of the present example further includes a plurality of elongate tabs (218) projecting laterally outwardly from deck (204) on each lateral side of cartridge body (202). Tabs (218) of the present example are spaced apart from one another in a longitudinal direction, and each tab (218) has a generally rounded rectangular shape. Cartridge body (202) further includes a plurality of attachment openings (220) spaced apart from one longitudinally on each side of elongate slot (206), with each attachment opening (220) being smaller than a staple opening (208) and having a hexagonal shape. In the present version, each tab (218) includes at least one attachment opening (220). Attachment openings (220) may be configured to facilitate releasable attachment of an adjunct, such as adjunct (230), to staple cartridge deck (204).

Adjunct (230) has a plurality of sub-structures in the form of three-dimensional, resiliently compressible (or collapsible) nodules (232) that define a lower portion of adjunct (230) and are integrally connected with one another, via an upper portion (233) of adjunct (230), in a plurality of linear arrays defining a lattice structure having an elongate rectangular shape.

Each nodule (232) of the present example has a generally cuboid shape defining four side surfaces (234), a lower surface (236), and an opening (238) in lower surface (236) that extends along a vertical central axis (A1) of nodule (232) and defines an open, hollow interior of nodule (232). Additionally, each nodule (232) is symmetrical about its centroid along a second axis (A2) of nodule (232) that extends horizontally in a proximal-distal direction parallel to the length of adjunct (230), and along a third axis (A3) of nodule (232) that extends horizontally in a direction traverse to the length of adjunct (230), where each axis (A1, A2, A3) extends through the centroid.

Adjunct (230) may be formed of an elastic, bioabsorbable polymeric material having a suitable degree of elasticity that enables adjunct (230) to compress and resiliently resume its original shape. In the present example, each nodule (232) of adjunct (230) is resiliently compressible in such a manner along at least each of its three axes (A1, A2, A3).

IV. Exemplary End Effectors Providing Consistent Compression on Variable Thickness Tissue In some instances, it may be desirable to provide an end effector and/or adjunct with one or more features for accommodating tissue having varying thickness while still providing substantially consistent compression on tissue along the length of the formed staple pattern. Exemplary versions of such end effectors and/or adjuncts are described in greater detail below. Unless otherwise described, it will be appreciated that such end effectors may be readily incorporated into instrument (10) in replacement of end effector (50) described above; and that such adjunct features may be applied to a multi-layer adjunct similar to buttress assemblies (110, 112) described above in connection with FIGS. 7-9, or alternatively to a compressible monolithic adjunct similar to adjunct (230) described above in connection with FIGS. 10-12.

A. Exemplary Buttress Assembly and End Effector having Barbed Fasteners

In some instances, it may be desirable to provide an end effector with an adjunct or combination of adjuncts capable of severing and stapling tissue to form a suitable and secure seal of tissue without forming a traditional "B" shaped staple. In other words, it may be desirable to provide an end effector with an adjunct or combination of adjuncts capable of severing and stapling tissue to form a suitable and secure seal of tissue without driving legs (126) of staples (80) against anvil (56) to bend legs (126) back into engagement with tissue ($T_1$, $T_2$) and/or buttress assembly (110). Further, as mentioned above, it may be desirable to utilize an adjunct (or combination of adjuncts) that are also configured to provide a consistent amount of compression on grasped tissue having variable thickness. FIGS. 13A-13E show an exemplary end effector (350) that may be readily incorporated into instrument (10) in replacement of end effector (50) described above. End effector (350) is substantially similar to end effector (50) described above, with differences elaborated below. In particular, rather than utilizing traditional staples (80) configured to form a traditional "B" shape in order to attach layers of recently severed tissue ($T_1$, $T_2$), end effector (350) utilizes fasteners (380) having a plurality of attachment features in the form of barbs (338) configured to suitably engage tissue ($T_1$, $T_2$) and buttress assembly (310) in order to attach severed tissue ($T_1$, $T_2$) and buttress assembly (310) together in response to firing end effector (350) in accordance with the description herein.

End effector (350) includes a lower jaw (352) and an upper jaw (354) which are substantially similar to lower jaw (52) and upper jaw (54) described above, with differences elaborated herein. Therefore, jaws (352, 354) are configured to pivot relative to each other in order to suitably grasp tissue ($T_1$, $T_2$) in accordance with the description herein.

Lower jaw (352) includes a replaceable cartridge (370) having a body (372), an upwardly facing deck (374), a plurality of fastener openings (378), a plurality of drivers (392), and a wedge sled (396); which may be substantially similar to body (72), upwardly facing deck (74), openings (78), staple drivers (82), wedge sled (86) described above, respectively, with differences elaborated herein. However, rather than having a plurality of staples (80) housed within openings (378) above a respective driver (392); replaceable cartridge (370) includes a plurality of fasteners (380) slidably housed within a respective opening (378). Fasteners (380) are configured to be driven upwardly towards upper jaw (354) by a respective driver (392) in response to distal actuation of wedge sled (396) in accordance with the description herein.

In the current aspect of the disclosure, fasteners (380) include a crown (382) and a pair of legs (384) extending upwardly from lateral ends of crown (382). Each leg (384) terminates into a piercing tip (386) suitable for piercing tissue ($T_1$, $T_2$) and buttress assembly (310) in accordance with the description herein. Legs (384) have sufficient column strength in order to support tip (386) while piercing tissue ($T_1$, $T_2$) and buttress assembly (310) without undesirably buckling and/or otherwise deforming. Additionally, each leg (384) includes a plurality of barbs (388). Each barb (388) extends laterally inward and downward from a perspective leg (384) and terminates into a point. As will be described in greater detail below, barbs (388) are oriented in order to accommodate fasteners (380) being driven into tissue ($T_1$, $T_2$) and buttress assembly (310) in a first direction; and inhibit fasteners (380) from dissociating with tissue ($T_1$, $T_2$) and buttress assembly (310) from falling out of tissue ($T_1$, $T_2$) and buttress assembly (310) in a second, opposite, direction. Therefore, fasteners (380) are configured to couple tissue ($T_1$, $T_2$) and buttress assembly (310) via barbs (388) such that legs (384) are not required to bend into a traditional "B" shaped staple formation. Since legs (384) are not required to be driven against an anvil in order to couple tissue ($T_1$, $T_2$) and buttress assembly (310), legs (384) may be shorter than legs (126) of traditional staples (80).

While barbs (388) extend laterally inwardly toward crown (382) in the current example, barbs (388) may extend from leg (384) in any suitable direction as would be apparent to one skilled in the art in view of the teachings herein. Further barbs (388) may have any suitable geometry as would be apparent to one skilled in the art in view of the teachings herein. For example, barbs (388) may extend annularly around leg (384). While fasteners (380) in the current aspects of the disclosure include a crown (382) extending between two legs (384), fasteners (380) may have any suitable structure as would be apparent to one skilled in the art in view of the teachings herein. For example, fastener (380) may include a single leg (384) with barbs (388) and a piecing tip (386).

Unlike upper jaw (54) described above, upper jaw (354) does not include an anvil defining plurality of staple forming pockets. Therefore, upper jaw (354) is not configured to engage legs (384) of fasteners (380) in order to bend fasteners (380) into a traditional "B" shaped staple formation. However, upper jaw (354) is configured to selectively attach to buttress assembly (310) in accordance with the description herein. Buttress assembly (310) may be repeatedly and easily loaded onto upper jaw (354) using any suitable means as would be apparent to one skilled in the art in view of the teaching herein, such as using a buttress applicator.

Buttress assembly (310) may be substantially similar to buttress assembly (110, 112) and/or adjunct (230) as described above, with differences elaborated below. Buttress assembly (310) includes a compressible buttress body (318), an adhesive layer (316) associated with an upper surface of compressible buttress body (318), and a mesh buttress body (314) associated with a lower surface of compressible buttress body (318).

Adhesive layer (316) is provided on buttress body (318) to adhere compressible buttress body (318) and mesh buttress body (314) to the underside of upper jaw (354). Such an adhesive material may provide proper positioning of compressible buttress body (318) and mesh buttress body (314) before and during actuation of end effector (350); then allow compressible buttress body (318) and mesh buttress body (314) to separate from end effector (350) after end effector (350) has been actuated, without causing damage to compressible buttress body (318) and mesh buttress body (314) that is substantial enough to compromise the proper subsequent functioning of compressible buttress body (318) and mesh buttress body (314). In some instances, buttress assembly (310) is attached to the underside of upper jaw (354) via a buttress applier cartridge during a procedure. In other instances, buttress assembly (310) may be attached to the underside of upper jaw (354) during manufacturing of end effector (350).

Compressible buttress body (318) of buttress assembly (310) may be substantially similar to buttress body (114) and/or adjunct (230) described above. Therefore, compressible buttress body (318) may be configured to provide structural reinforcement to the lines of fasteners (380) formed in tissue ($T_1$, $T_2$). Additionally, or alternatively, compressible buttress body (318) may be configured to apply a compression spring force to stapled tissue consistently along the entire length of the formed fastener pattern, thereby ensuring a secure seal of tissue having a thickness that varies along a length of the formed fastener pattern and end effector (350). It should be understood that compressible buttress body (318) may be configured to provide any other suitable benefit as would be apparent to one skilled in the art in view of the teachings herein.

As mentioned above, mesh buttress body (314) is associated with the with a lower surface of compressible buttress body (318). In particular, mesh buttress body (314) is positioned on compressible buttress body (318) in order to engage tissue ($T_1$, $T_2$) as jaws (352, 354) pivot toward each other in accordance with the description herein. While mesh buttress body (314) may not be configured to compress like buttress body (318), mesh buttress body (314) is suitably compliant in order to deform its profile with compressible buttress body (318) in response to grasping tissue ($T_1$, $T_2$) with varying thickness in accordance with the description herein. Therefore, mesh buttress body (318) may maintain suitable engagement with compressible buttress body (318) while compressible buttress body (318) deforms in response to grasping tissue ($T_1$, $T_2$) with varying thickness.

Mesh buttress body (314) may be thinner than compressible buttress body (318). Mesh buttress body (314) is configured to engage barbs (388) of fasteners (380) such that after end effector (350) is fired, engagement between barbs (388) and mesh buttress body (314) help inhibit fasteners (380) from dissociation with tissue ($T_1$, $T_2$) and buttress assembly (310); and help substantially maintain at least some of the compressive forces buttress assembly (310) applied to tissue ($T_1$, $T_2$) via closure of jaws (352, 354), even after jaws (352, 354) suitably release tissue ($T_1$, $T_2$) and buttress assembly (310) in accordance with the description herein. Mesh buttress body (314) may have any suitable geometry as would be apparent to one skilled in the art in view of the teachings herein. Further, mesh buttress body (314) may be formed of any suitable material as would be apparent to one skilled in the art in view of the teachings herein.

While barbs (388) are configured to mechanically latch tissue ($T_1$, $T_2$) and buttress assembly (310) in the current example, this is merely optional. In some instances, initial interaction between legs (384) and buttress bodies (314, 318) may cause a chemical reaction that helps attach tissue ($T_1$, $T_2$) and buttress assembly (310) in accordance with the description herein. In some instances, initial interaction between legs (384) and buttress bodies (314, 318) may cause an energy reaction that helps attach tissue ($T_1$, $T_2$) and buttress assembly (310) in accordance with the description herein. For example, compressible buttress body (318) may include a silver impregnated cushion layer charged with energy that shorts out on fastener (380), thereby producing heat that bonds tips (386) to the compressible buttress body (318).

Figure 13A:
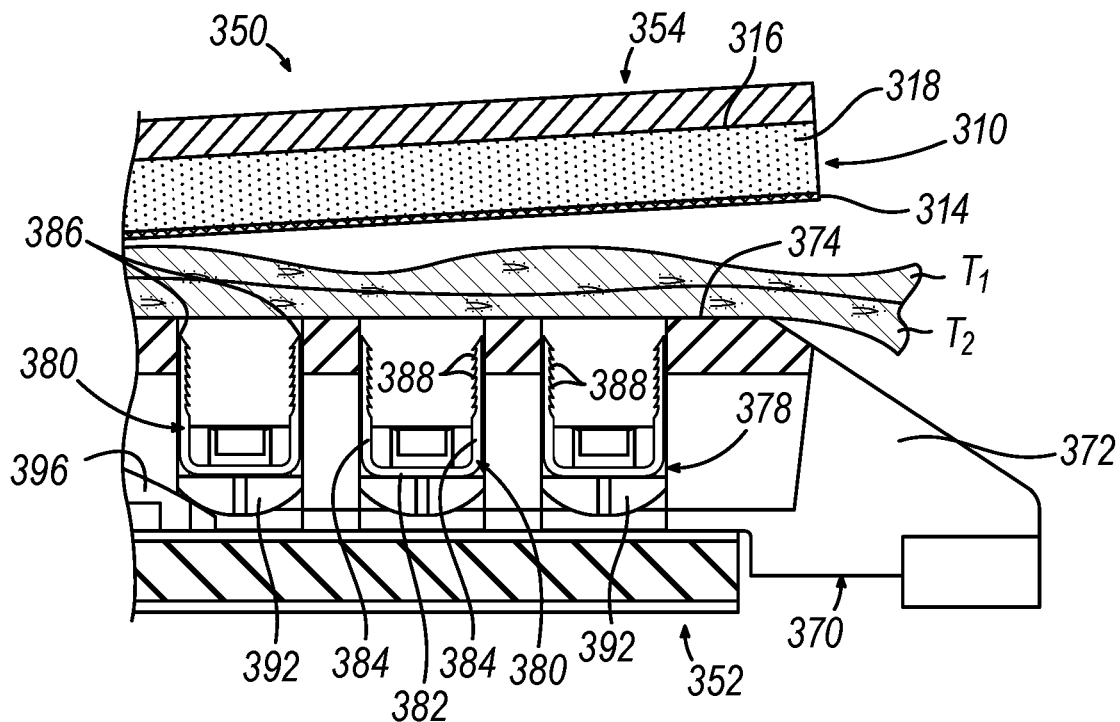
FIG. 13A depicts a side cross-sectional view of an alternative end effector and buttress assembly, with jaws in the open position.
Figure 13B:
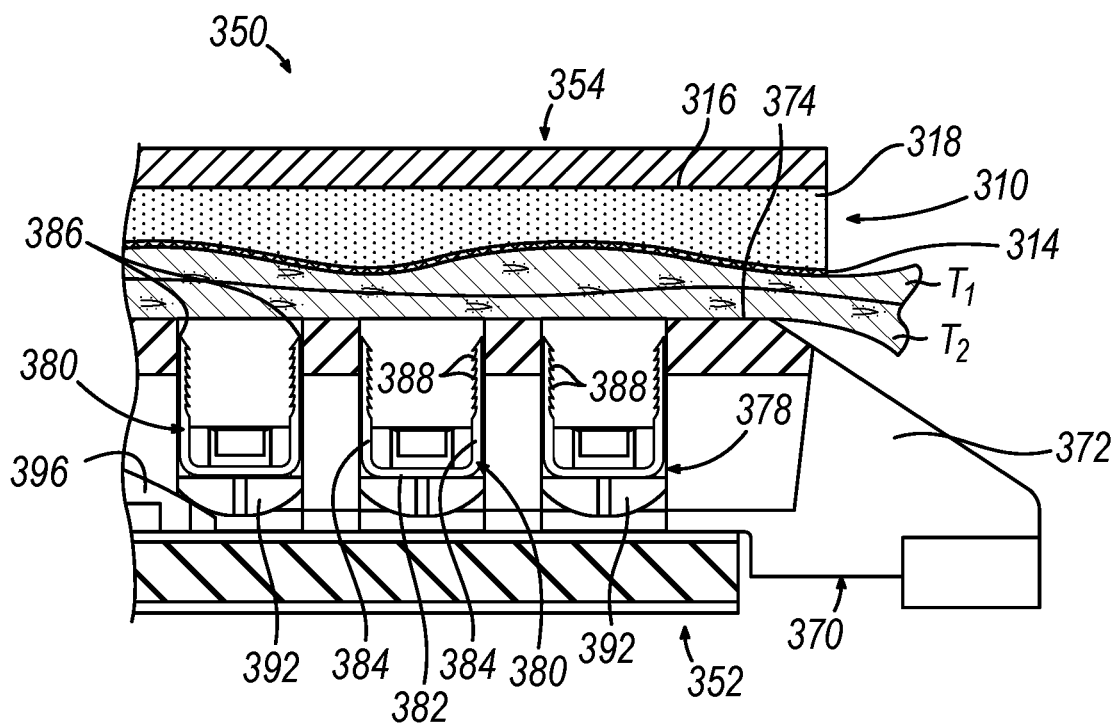
FIG. 13B depicts a side cross-sectional view of the end effector and buttress assembly of FIG. 13A, with jaws in the closed position grasping tissue.
Figure 13C:
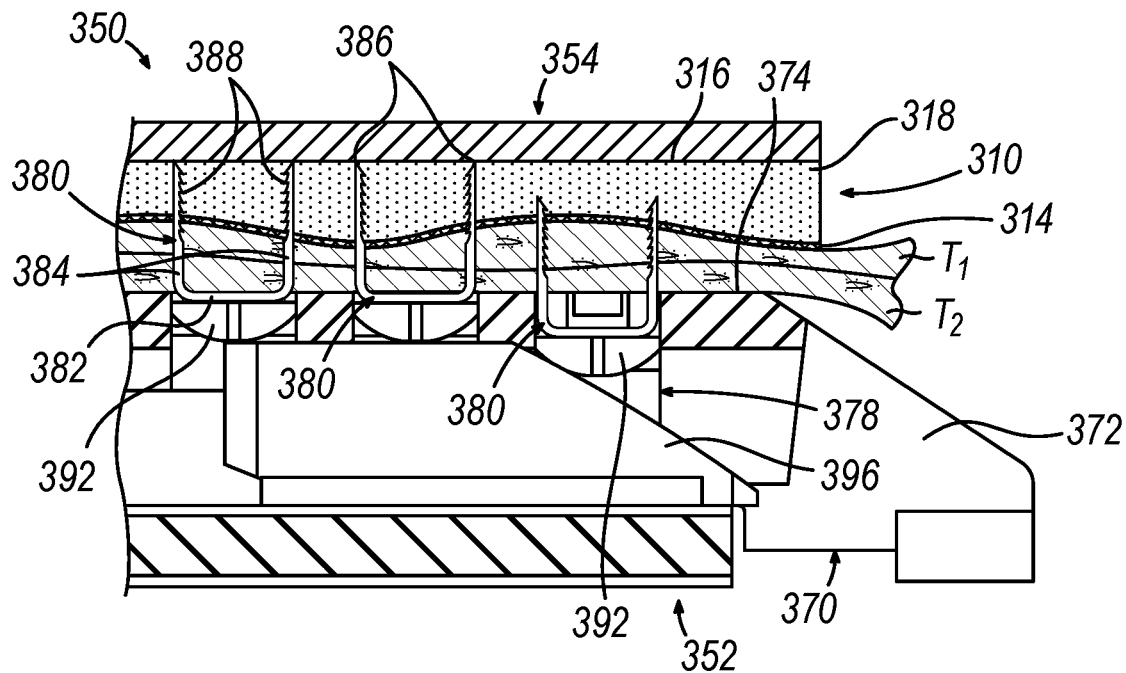
FIG. 13C depicts a side cross-sectional view of the end effector and buttress assembly of FIG. 13A, with jaws in the closed position grasping tissue and a wedge sled of the end effector actuated distally to drive a plurality of fasteners into grasped tissue and the buttress assembly.
Figure 13D:
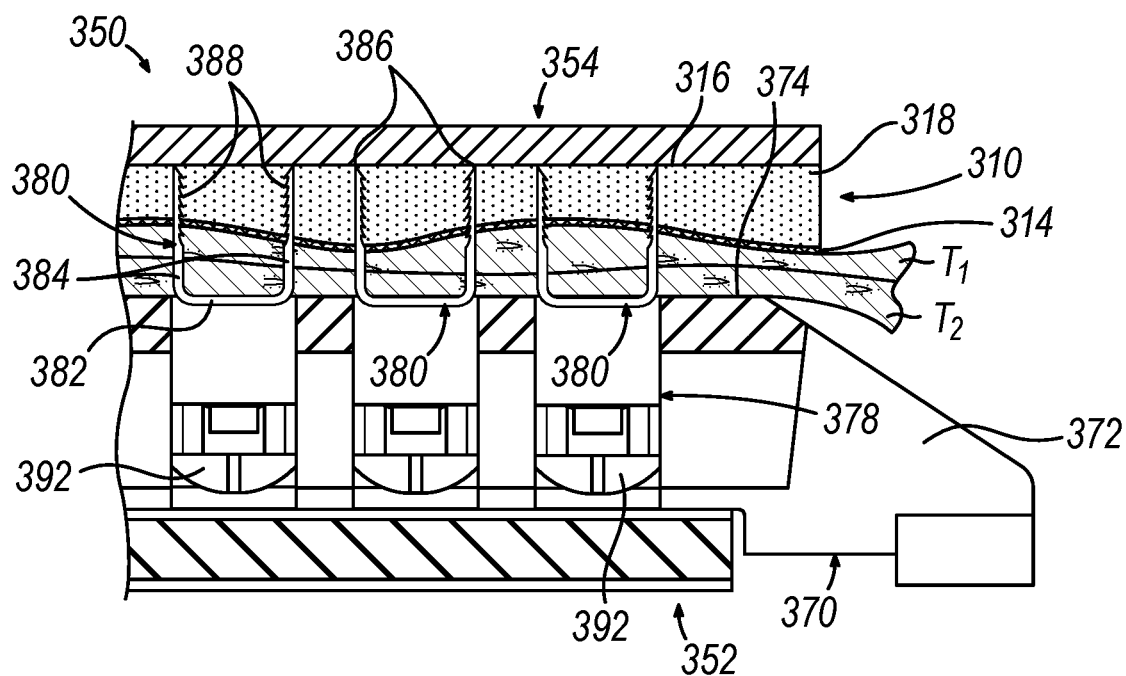
FIG. 13D depicts a side cross-sectional view of the end effector and buttress assembly of FIG. 13A, with jaws in the closed position grasping tissue and the plurality of fasteners driven into grasped tissue and the buttress assembly.
Figure 13E:
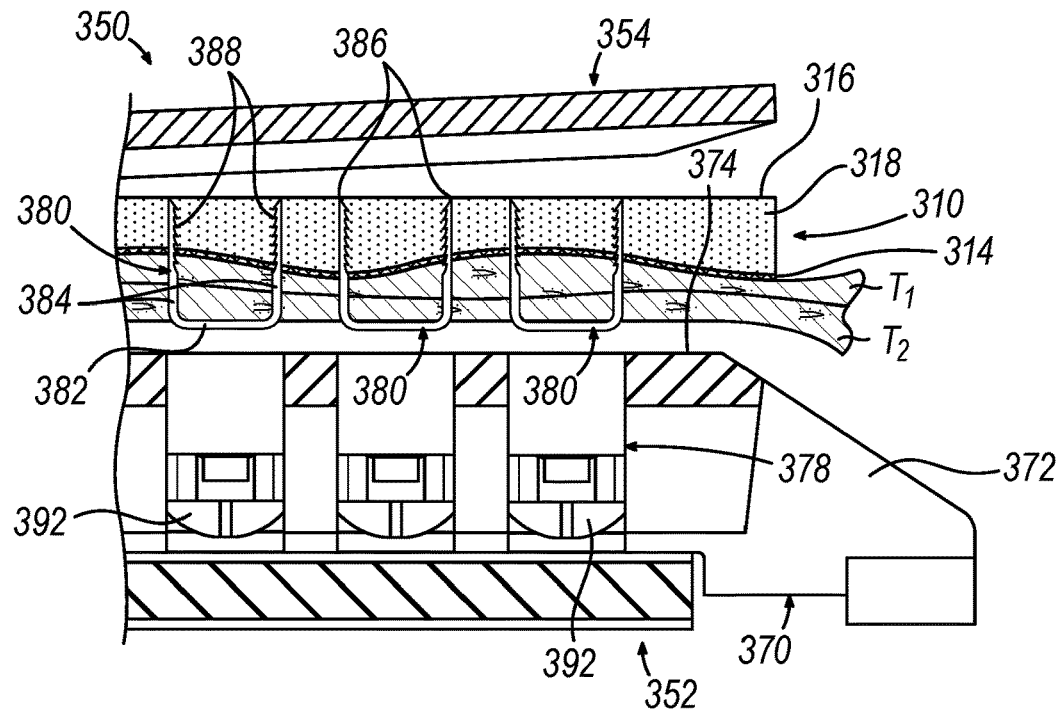
FIG. 13E depicts a side cross-sectional view of the end effector and buttress assembly of FIG. 13A, with jaws in the open position, thereby releasing the grasped tissue, buttress assembly, and plurality of fasteners.
Figure 14:
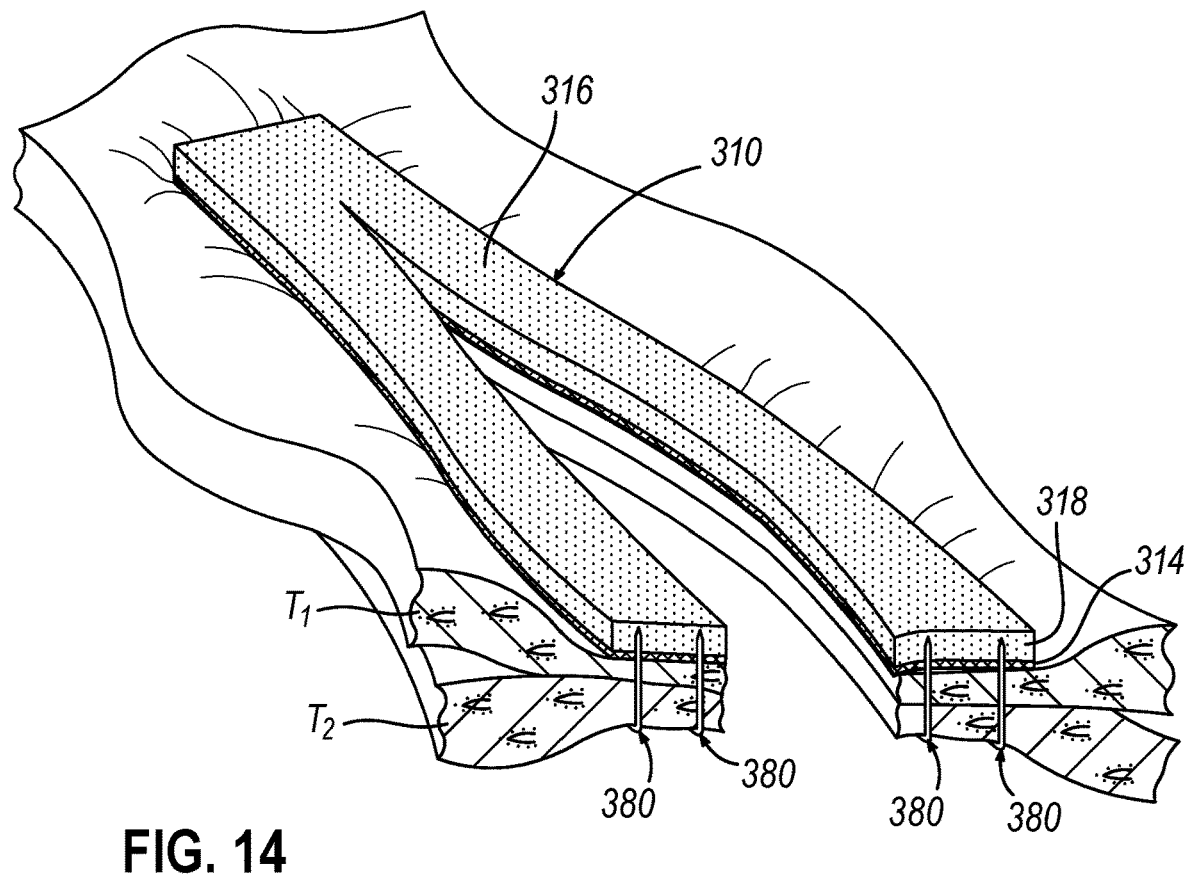
FIG. 14 depicts a perspective view of severed and stapled tissue utilizing the end effector and the buttress assembly of FIG. 13A.

FIGS. 13A-13E show an exemplary use of end effector (350) in order to staple and sever tissue ($T_1$, $T_2$) in accordance with the teaches herein, while FIG. 14 shows an end result of exemplary use of end effector (350). First, as shown in FIG. 13A, jaws (352, 354) and buttress assembly (310) may be positioned such that tissue ($T_1$, $T_2$) is interposed between jaws (352, 354) in the open position. Next, as shown in FIG. 13B, jaws (352, 354) and buttress assembly (310) may suitably grasp tissue ($T_1$, $T_2$). In the current example, tissue ($T_1$, $T_2$) has varying thickness along the length of jaws (352, 354) and buttress assembly (310). Therefore, compressible buttress body (318) may compress as shown in FIG. 13B in order to apply substantially consistent compression on the portion of tissue ($T_1$, $T_2$) grasped by jaws (352, 354). Additionally, mesh buttress body (314) also conforms to suitably engage tissue ($T_1$, $T_2$) and remain in engagement with compressible buttress body (318).

Once tissue ($T_1$, $T_2$) is grasped and ready to be severed and stapled, end effector (350) may be fired in accordance with the description herein. Therefore, as shown in FIG. 13C, wedge sled (396) may be actuated distally in similar fashion as wedge sled (86) described above, thereby actuating drivers (392) upward within a respective opening (378). As shown between FIGS. 13C and 13D, since fasteners (380) are suitably engaged with a respective driver (392), fasteners (380) are driven upward out of openings (378). It should be understood that end effector (350) also severs tissue ($T_1$, $T_2$) while actuating drivers (392) upwardly in a similar fashion as end effector (50) described above.

While fasteners (380) are driven upward out of openings (378), piercing tips (386) pierce tissue ($T_1$, $T_2$), mesh buttress body (314) and compressible buttress body (318), thereby allowing legs (384) to extend within tissue ($T_1$, $T_2$) and buttress bodies (314, 318). Fastener (380) may be driven upward until crown (382) suitably abuts against a respective layer of tissue ($T_1$, $T_2$). In some instances, crown (382) may rest flush against a respective layer of tissue ($T_1$, $T_2$).

As mentioned above, barbs (388) are oriented to accommodate for legs (384) to be driven upward into tissue ($T_1$, $T_2$), through mesh buttress body (314), and into compressible buttress body (318). Additionally, barbs (388) are oriented to engage surrounding structures (i.e. tissue ($T_1$, $T_2$) and buttress bodies (314, 318)) to inhibit fasteners (380) from dissociating with buttress bodies (314, 318) and tissue ($T_1$, $T_2$). The height at which barbs (388) engage mesh buttress body (314) may be determined by both the compression of adjacent portions of compressible buttress body (318) and the thickness of adjacent tissue ($T_1$, $T_2$). Additionally, as mentioned above, barbs (388) allow fasteners (380) to couple tissue ($T_1$, $T_2$) with buttress bodies (314, 318) without having to form a traditional "B" shaped staple, thereby allowing legs (384) to be shorter than legs (126) of staple (80).

As shown in FIG. 13D, after fasteners (380) have been suitably fired, jaws (352, 354) may still be imparting a compressive force onto both buttress assembly (310) and tissue ($T_1$, $T_2$). However, as shown in FIGS. 13E and 14, after jaws (352, 354) are opened to release recently served and fastened tissue ($T_1$, $T_2$), engagement between barbs (388) and surrounding structures may maintain a suitable compressive force such that buttress assembly (310) maintains suitable contact with tissue ($T_1$, $T_2$), even if tissue ($T_1$, $T_2$) deviates in thickness. Maintaining suitable contact between buttress assembly (310) and tissue ($T_1$, $T_2$) may promote the structural integrity of recently fastened tissue ($T_1$, $T_2$), sealing of recently severed tissue ($T_1$, $T_2$), and any other suitable benefits as would be apparent to one skilled in the art in view of the teachings herein.

Additionally, barbs (388) may engage a respective portion of mesh buttress body (314) in order to further promote the suitable compressive forces necessary for buttress assembly (310) to remain suitably engaged with tissue ($T_1$, $T_2$) after jaws (352, 354) release tissue. Therefore, engagement between barbs (388) and mesh buttress body (314) may enhance buttress assemblies (310) attachment with tissue ($T_1$, $T_2$) via fasteners (380).

While buttress assembly (310) is associated with upper jaw (354) in the current aspect of the disclosure, this is merely optional. In some instances, buttress assembly (310) may be associated with deck (374) of lower jaw (352).

In some instances, it may be desirable to further promote the coupling between recently severed tissue ($T_1$, $T_2$) and buttress assembly (310) via use of additional fasteners. FIGS. 15A-15E show an exemplary alternative buttress assembly (320) incorporated into end effector (350) in replacement of buttress assembly (310) described above. Buttress assembly (320) is substantially similar to buttress assembly (310) described above, with differences elaborated below. In particular, buttress assembly (320) comprises a plurality of complementary internal fasteners (330) initially housed within compressible buttress body (328); where internal fasteners (330) are configured to further promote the attachment between buttress assembly (320) and tissue ($T_1$, $T_2$).

Buttress assembly (320) includes a mesh buttress body (324), an adhesive layer (326), and a compressible buttress body (328); which may be substantially similar to mesh buttress body (314), adhesive layer (316), and compressible buttress body (318) described above, with difference elaborated below. Complementary internal fasteners (330) may be substantially similar to fasteners (380) described above, except internal fasteners (330) are housed initially housed within compressible buttress body (328). Therefore, internal fasteners (330) each include a crown (332), legs (334), piercing tips (336), and a plurality of barbs (338); which may be substantially similar to crown (382), legs (384), piercing tips (386), and plurality of barbs (388) described above, with differences describe herein.

Crown (322) of fasteners (330) are located adjacent to adhesive layer (326) such that as jaws (352, 354) close in order to grasp tissue ($T_1$, $T_2$) in accordance with the description herein, the underside of upper jaw (354) supports each internal fastener (330) via engagement with crown (322). Therefore, as jaws (352, 354) are closed to grasp tissue ($T_1$, $T_2$), some piercing tips (336) may pierce through compressible buttress body (318), mesh buttress body (314) and tissue ($T_1$, $T_2$) in response to buttress body (318) compressing to accommodate for tissue ($T_1$, $T_2$) with varying thickness. In instance where piercing tip (336) does pierce through at least some portion of tissue ($T_1$, $T_2$), barbs (338) may suitably grasp tissue (T₁, T₂), mesh buttress body (314), and compressible buttress body (328) to further promote the coupling between tissue (T₁, T₂) and buttress assembly (320). Therefore, barbs (338) may inhibit the portion of tissue (T₁, T₂) penetrated by piercing tips (336) from dissociating with buttress assembly (320) after end effector (350) is suitably fired in accordance with the description herein.

Fasteners (330) are positioned within compressible buttress body (328) such that when jaws (352, 354) are in the closed position, legs (334) of internal fasteners (330) associated with buttress assembly (320) and legs (384) of fasteners (380) are longitudinally offset from each other. However, crown (332) of complementary fasteners (330) are laterally aligned with piercing tips (386) of fasteners (380) such that once suitably deployed, crown (332) and legs (334) may act as a protective sheath for piercing tips (386); while crown (382) and legs (384) may act as a protective sheath for piercing tips (336). Therefore, fasteners (330, 380) are aligned in a longitudinally offset relationship such that piercing tips (386, 336) are covered to inhibit piercing tips (386, 336) from invertedly damaging adjacent anatomy not intended to interact with tips (386, 336).

Figure 15A:
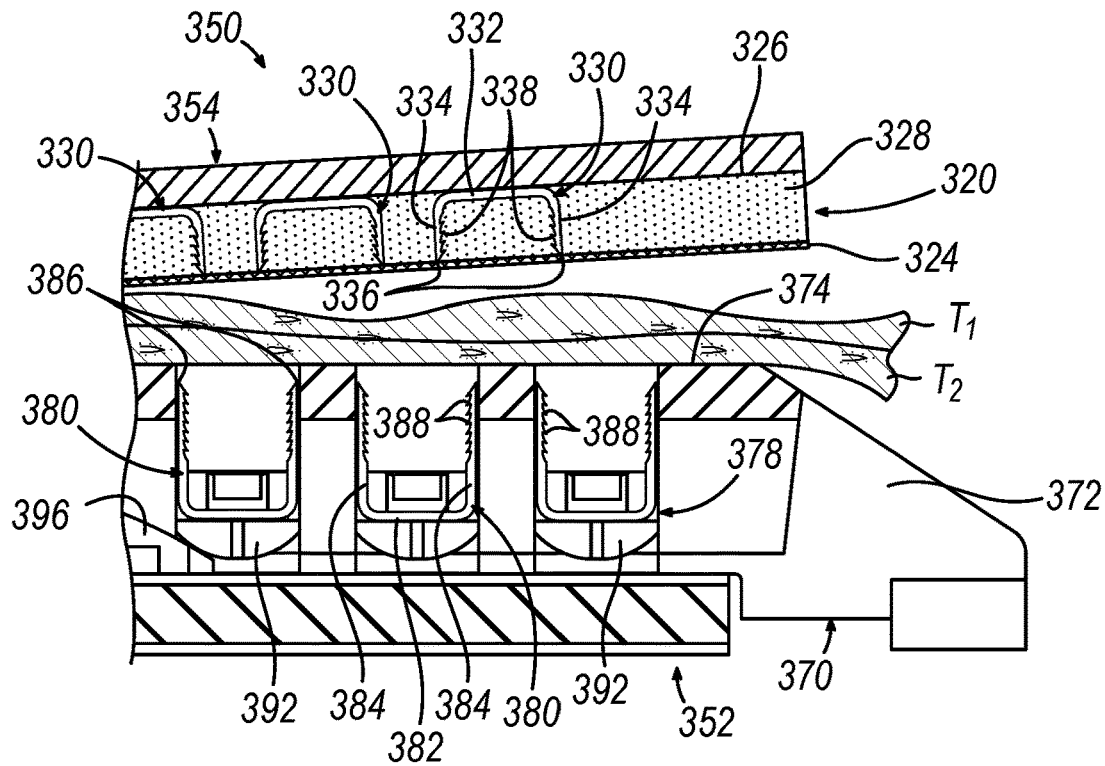
FIG. 15A depicts a side cross-sectional view of an alternative end effector and buttress assembly, with jaws in the open position.
Figure 15B:
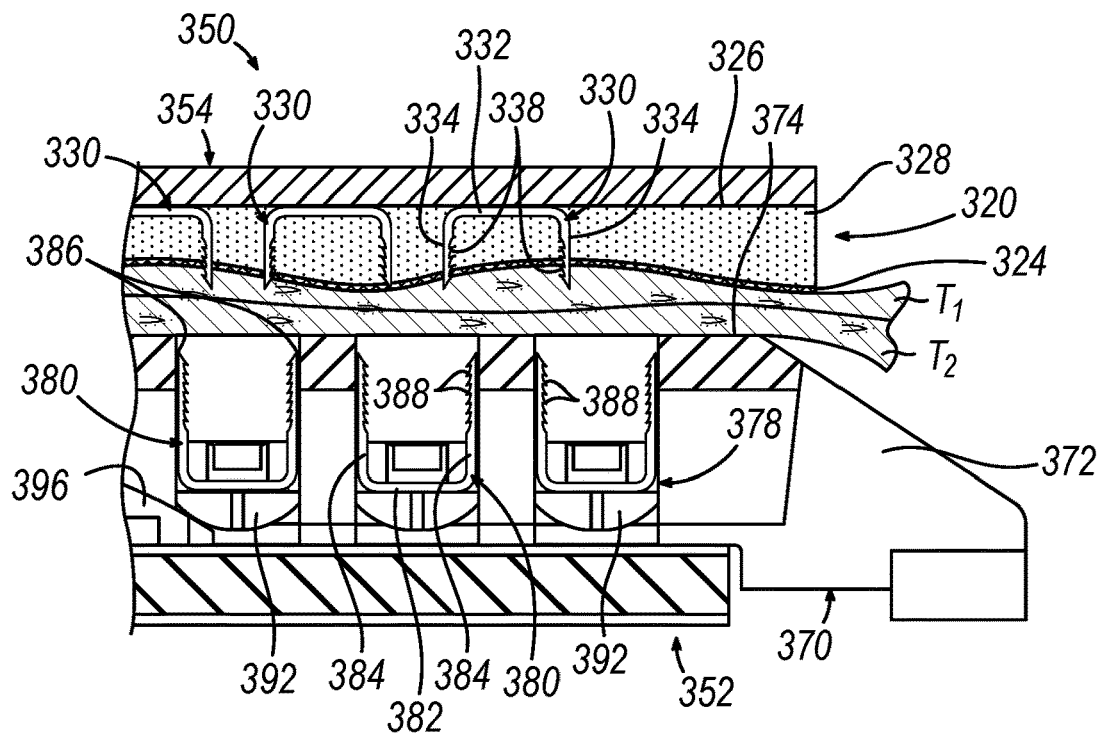
FIG. 15B depicts a side cross-sectional view of the end effector and buttress assembly of FIG. 15A, with jaws in the closed position grasping tissue.

FIGS. 15A-15E show an exemplary use of end effector (350) incorporating buttress assembly (320). First, as shown in FIG. 15A, jaws (352, 354) and buttress assembly (320) may be positioned such that tissue (T₁, T₂) is interposed between jaws (352, 354) in the open position. Next, as shown in FIG. 15B, jaws (352, 354) and buttress assembly (320) may suitably grasp tissue (T₁, T₂). In the current example, tissue (T₁, T₂) has varying thickness along the length of jaws (352, 354) and buttress assembly (320). Therefore, compressible buttress body (328) may compress as shown in FIG. 15B in order to apply substantially consistent compression on the portion of tissue (T₁, T₂) grasped by jaws (352, 354). Mesh buttress body (324) also conforms to suitably engage tissue (T₁, T₂) and remain in engagement with compressible buttress body (328). Additionally, since the underside of upper jaw (354) suitably supports internal fasteners (330), some piercing tips (336) of internal fasteners (330) are driven through compressible buttress body (328), mesh buttress body (324), and tissue (T₁, T₂), thereby promoting the attachment of buttress assembly (320) to tissue (T₁, T₂).

Figure 15C:
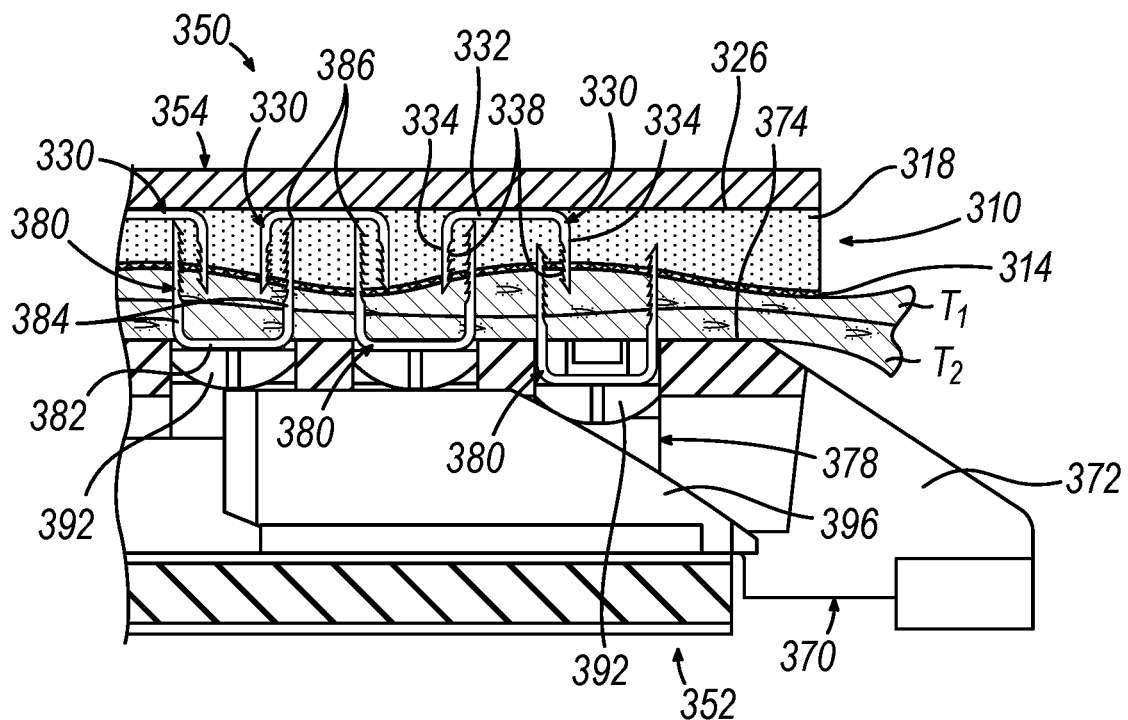
FIG. 15C depicts a side cross-sectional view of the end effector and buttress assembly of FIG. 15A, with jaws in the closed position grasping tissue and a wedge sled of the end effector actuated distally to drive a plurality of fasteners into grasped tissue and the buttress assembly.

Once tissue (T₁, T₂) is grasped and ready to be severed and stapled, end effector (350) may be fired in accordance with the description herein. Therefore, as shown in FIG. 15C, wedge sled (396) may be actuated distally in similar fashion as wedge sled (86) described above, thereby actuating drivers (392) upward within a respective opening (378). As shown between FIGS. 15C and 15D, since fasteners (380) are suitably engaged with a respective driver (392), fasteners (380) are driven upward out of openings (378). It should be understood that end effector (350) also severs tissue (T₁, T₂) while actuating drivers (392) upwardly in a similar fashion as end effector (50) described above.

While fasteners (380) are driven upward out of openings (378), piercing tips (386) pierce tissue (T₁, T₂), mesh buttress body (324) and compressible buttress body (328), thereby allowing legs (384) to extend within tissue (T₁, T₂) and buttress bodies (314, 318). Fastener (380) may be driven upward until crown (382) suitably abuts against a respective layer of tissue (T₁, T₂). In some instances, crown (382) may rest flush against a respective layer of tissue (T₁, T₂). Additionally, each piercing tip (386, 336) is protected between an adjacent fastener (330, 380) associated with the opposing jaw (352, 354).

Barbs (388, 338) of each fastener (330, 380) are oriented to engage surrounding structures (i.e. tissue (T₁, T₂) and buttress bodies (324, 328)) to inhibit fasteners (380, 330) from dissociating with buttress bodies (324, 328) and tissue (T₁, T₂). The height at which barbs (388, 338) engage mesh buttress body (324) may be determined by both the compression of adjacent portions of compressible buttress body (328) and the thickness of adjacent tissue (T₁, T₂).

Figure 15D:
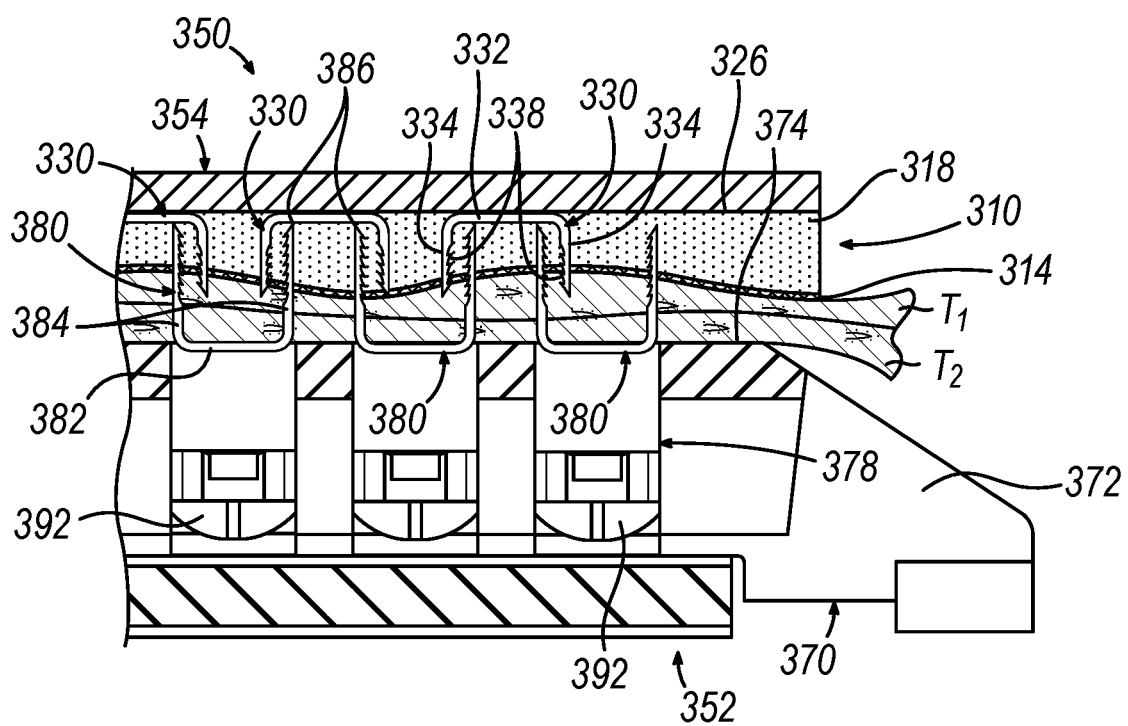
FIG. 15D depicts a side cross-sectional view of the end effector and buttress assembly of FIG. 15A, with jaws in the closed position grasping tissue and the plurality of fasteners driven into grasped tissue and the buttress assembly.
Figure 15E:
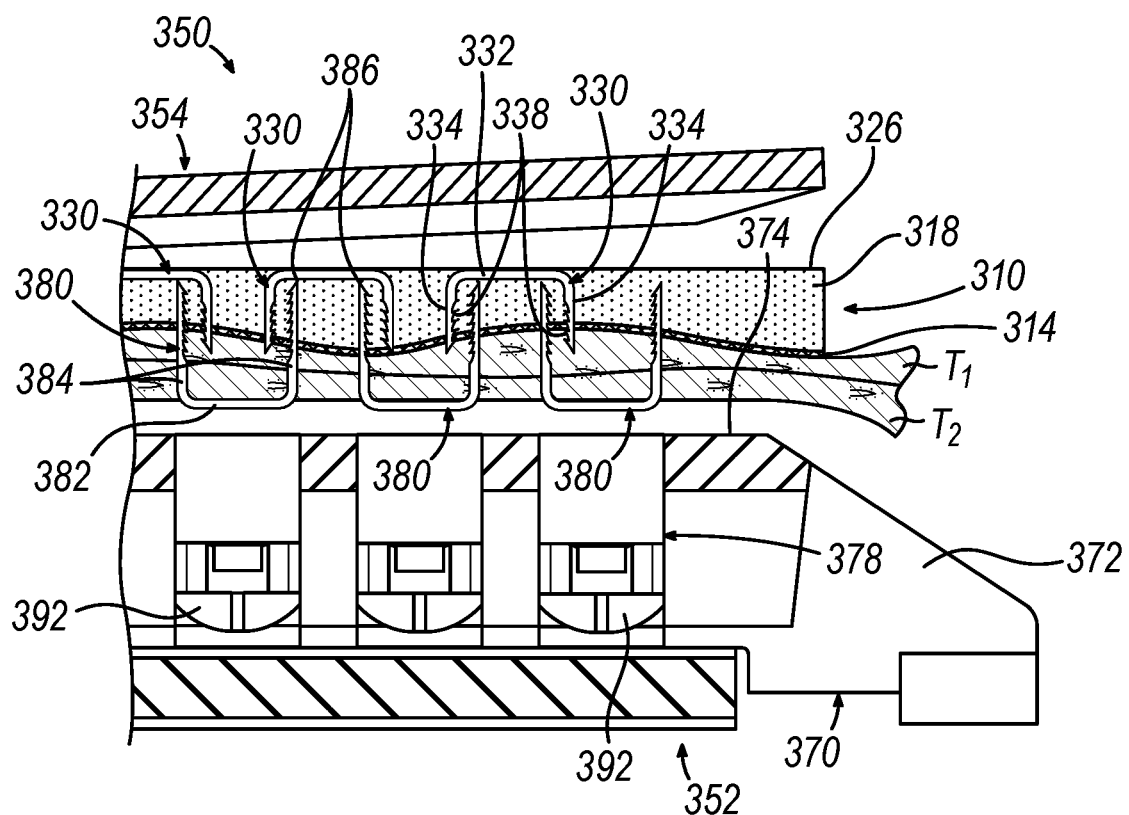
FIG. 15E depicts a side cross-sectional view of the end effector and buttress assembly of FIG. 15A, with jaws in the open position, thereby releasing the grasped tissue, buttress assembly, and plurality of fasteners.

As shown in FIG. 15D, after fasteners (380) have been suitably fired, jaws (352, 354) may still be imparting a compressive force onto both buttress assembly (320) and tissue (T₁, T₂). However, as shown in FIGS. 15E, after jaws (352, 354) are opened to release recently served and fastened tissue (T₁, T₂), engagement between barbs (388) and surrounding structures may maintain a suitable compressive force such that buttress assembly (320) maintains suitable contact with tissue (T₁, T₂), even if tissue (T₁, T₂) deviates in thickness. Barbs (338) of fasteners (330) also provide additional support to help ensure buttress assembly (320) maintains suitable engagement with tissue (T₁, T₂). Maintaining suitable contact between buttress assembly (320) and tissue (T₁, T₂) may promote the structural integrity of recently fastened tissue (T₁, T₂), sealing of recently severed tissue (T₁, T₂), and any other suitable benefits as would be apparent to one skilled in the art in view of the teachings herein.

Additionally, barbs (338) may engage a respective portion of mesh buttress body (324) in order to further promote the suitable compressive forces necessary for buttress assembly (320) to remain suitably engaged with tissue (T₁, T₂) after jaws (352, 354) release tissue. Therefore, engagement between barbs (338) and mesh buttress body (324) may enhance buttress assemblies (310) attachment with tissue (T₁, T₂) via fasteners (330).

Figure 16A:
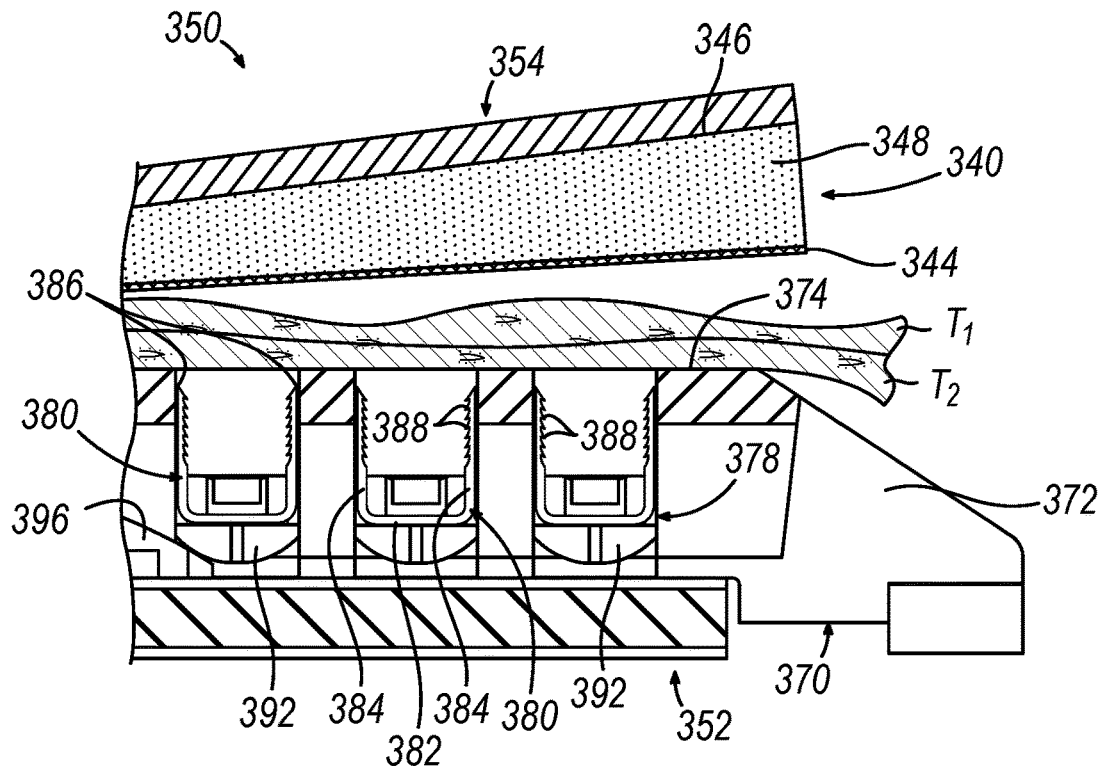
FIG. 16A depicts a side cross-sectional view of an alternative end effector and buttress assembly, with jaws in the open position.
Figure 16B:
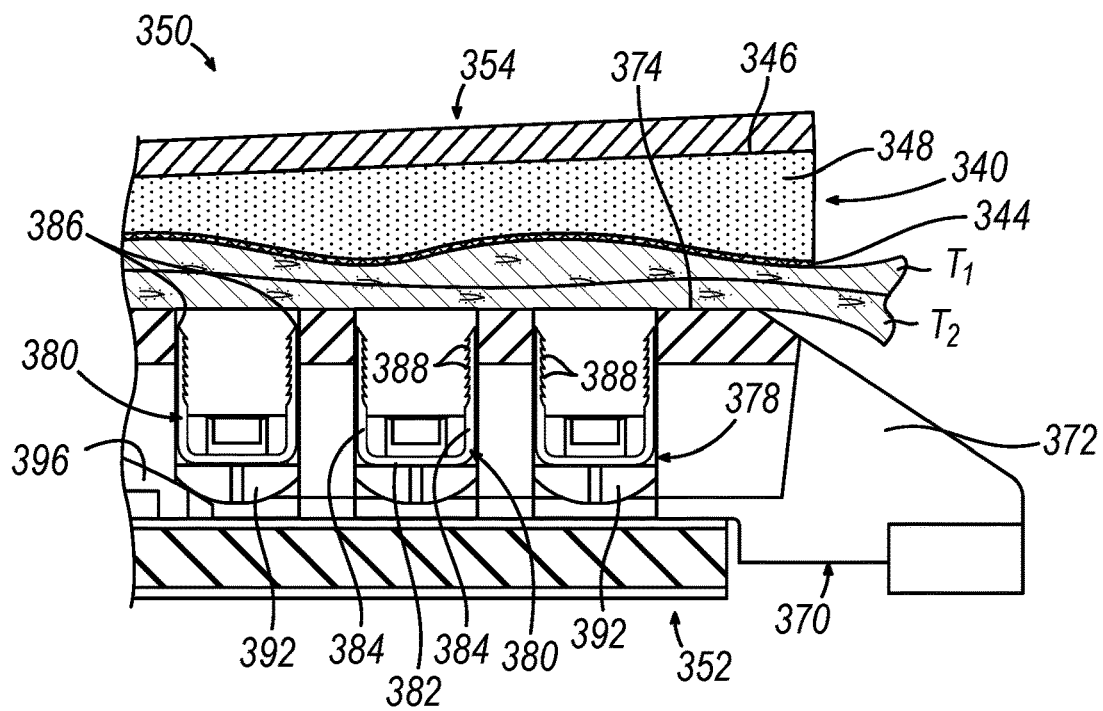
FIG. 16B depicts a side cross-sectional view of the end effector and buttress assembly of FIG. 16A, with jaws in the closed position grasping tissue.

In some instances, is may be desirable to suitably fire end effector (350) such that fasteners (380) may attach to buttress assembly (310) and tissue (T₁, T₂) without requiring jaws (352, 354) being closed to such a degree that jaws (352, 354) are substantially parallel with each other. FIGS. 16A-16B show an example alternative buttress assembly (340) that may be readily incorporated into end effector (350) in replacement of buttress assembly (310) described above. Buttress assembly (340) is substantially similar to buttress assembly (310) described above, with differences elaborated below.

Buttress assembly (340) includes a mesh buttress body (344), an adhesive layer (346), and a compressible buttress body (348); which may be substantially similar to mesh buttress body (314), adhesive layer (316), and compressible buttress body (318) described above, with difference elaborated below. Compressible buttress body (348) is tapered such that compressible buttress body (348) is thicker toward the distal end of end effector (350) compared to the proximal end of end effector (350). In the present aspect of the disclosure, the tapered thickness of compressible buttress body (348) is substantially linear such that compressible buttress body (348) forms a wedge shape. As shown between FIGS. 16A-16B, the change in thickness of compressible buttress body (348) allows jaws (352, 354) to suitably grasp tissue (T₁, T₂) without requiring jaws (352, 354) to extend substantially parallel relative to each other. Therefore, end effector (350), while incorporating buttress assembly (340), may be fired in order to suitably sever and fasten tissue (T₁, T₂) to buttress assembly (340) without requiring jaws (352, 354) to be fully closed; while still allowing fasteners (380) to apply the correct amount of pressure such that buttress assembly (340) and ($T_1$, $T_2$) maintain suitably engagement with each other after end effector (350) is fired.

B. Exemplary End Effector having Spring Loaded Staple Drivers and Segmented Cartridge Deck In some instances, it may be desirable to provide a consistent amount of compression on grasped tissue having variable thickness without the necessary incorporation of an adjunct. FIGS. 17A-17D show an example end effector (450) configured to provide substantially consistent compression on grasped tissue having variable thickness.

End effector (450) may be readily incorporated into instrument (10) in replacement of end effector (50) described above. End effector (450) may be substantially similar to the effector (50), except for the differences described herein. Therefore, end effector (450) includes a lower jaw (452), an upper jaw (454), an anvil (456) defining a plurality of staple forming pockets (458), a replaceable cartridge (470), a body (472), an upwardly extending deck (474), and a wedge sled (486); which may be substantially similar to lower jaw (52), upper jaw (54), anvil (56), staple forming pockets (58), replaceable cartridge (70), body (72), upwardly extending deck (74), and wedge sled (86) described above, respectively, with differences elaborated below. In particular, upwardly extending deck (474) is separated into a plurality of pressure loaded sections (476) that are configured to adjust their heights relative to each other in response to jaws (452, 452) grasping tissue with varying thickness.

Pressure loaded sections (476) each define a respective opening (478) that slidably houses a staple (80) and compressible staple driver (410). Compressible staple driver (410) may be substantially similar to staple driver (82), with differences elaborated herein. Therefore, wedge sled (486) is configured to actuate distally within body (472) to thereby cam against compressible staple driver (410) in order to actuate staple (80) upward within opening (478) to thereby drive staple (80) through tissue ($T_1$, $T_2$) and against staple forming pockets (458) to form a traditional "B" shaped fired staple (80).

Each pressure loaded section (476) is resiliently biased into a position such that upward facing deck (474) forms a substantially flat, planar, surface. In the current aspect of the disclosure, pressure loaded sections (476) are biased toward the position shown in FIG. 17A. As best shown between FIGS. 17A-17B, pressure loaded sections (476) are configured to vertically compress in response to jaws (452, 454) grasping tissue ($T_1$, $T_2$) having varying thickness. Therefore, pressure loaded sections (476) may be configured to provide substantially uniform compression on tissue ($T_1$, $T_2$) having varying thickness without requiring the use of adjuncts or buttress assemblies. Pressure loaded sections (476) may inhibit over clamping and potentially damaging tissue ($T_1$, $T_2$). Pressure loaded sections (476) may include any suitable components as would be apparent to one skilled in the art in view of the teachings herein.

Additionally, as shown in FIGS. 18 and 22A-23B, end effector (450) includes a plurality of compressible staple drivers (410) configured to vary the staple height of a traditional "B" formed fired staple (80) depending on the thickness of tissue ($T_1$, $T_2$) directly adjacent to a respective staple (80). Therefore, staple drivers (410) are configured to work in conjunction with pressure loaded section (476) to adjust the staple height of a traditional "B" shaped fired staple (80) such that staple (80) suitably engages tissue via crown (122) and legs (126). Compressible staple drivers (410) each include a sled engagement body (414), a staple engagement body (414), and a biasing body (416) interposed between the sled engagement body (414) and the staple engagement body (414). Sled engagement body (414) is configured to suitably engage wedge sled (486) in accordance with the description herein, while staple engagement body (414) is configured to abut against crown (122) of staple (80) to thereby drive staple (80) against anvil (456) in accordance with the description herein.

When driving staples (80) through thicker tissue ($T_1$, $T_2$), more force may be required to suitably from a traditional "B" formed fired staple (80) as compared to driving staples (80) through thinner tissue ($T_1$, $T_2$). As shown between FIGS. 22A-23B, biasing body (416) is configured to suitably deform in response to attempting to drive a corresponding staple (80) through thicker tissue ($T_1$, $T_2$) as compared to thinner tissue, therefore altering the distance a fired staple (80) staples travels, which may in turn determine the final staple height of the traditional "B" formed staple.

FIGS. 22A-22B show compressible staple driver (410) driving a corresponding staple (80) through thinner tissue ($T_1$, $T_2$). Since the force required to drive the staple through thinner tissue ($T_1$, $T_2$) is relatively lower compared to thicker tissue, biasing body (416) does not overly compress during the firing process. Since biasing body (416) does not overly compress, the length of compressible staple driver (410) may remain substantially the same length as compared to when in the pre-fired position. Therefore, staple driver (410) may drive staple (80) a further distance out of staple opening (478) as compared to when staple driver (410) is compressed. It should also be understood that when jaws (452, 454) suitably grasp thinner tissue ($T_1$, $T_2$), the gap between the corresponding pressure loaded section (476) and anvil (456) is smaller compared to when grasping thicker tissue ($T_1$, $T_2$). Therefore, with staple (80) being fired a further distance out of opening (478), and the gap between anvil (456) and corresponding pressure loads section (476) being smaller, the final staple height of the traditional "B" formed staple may be smaller in order to suitably engage thinner tissue ($T_1$, $T_2$).

Figure 23B:
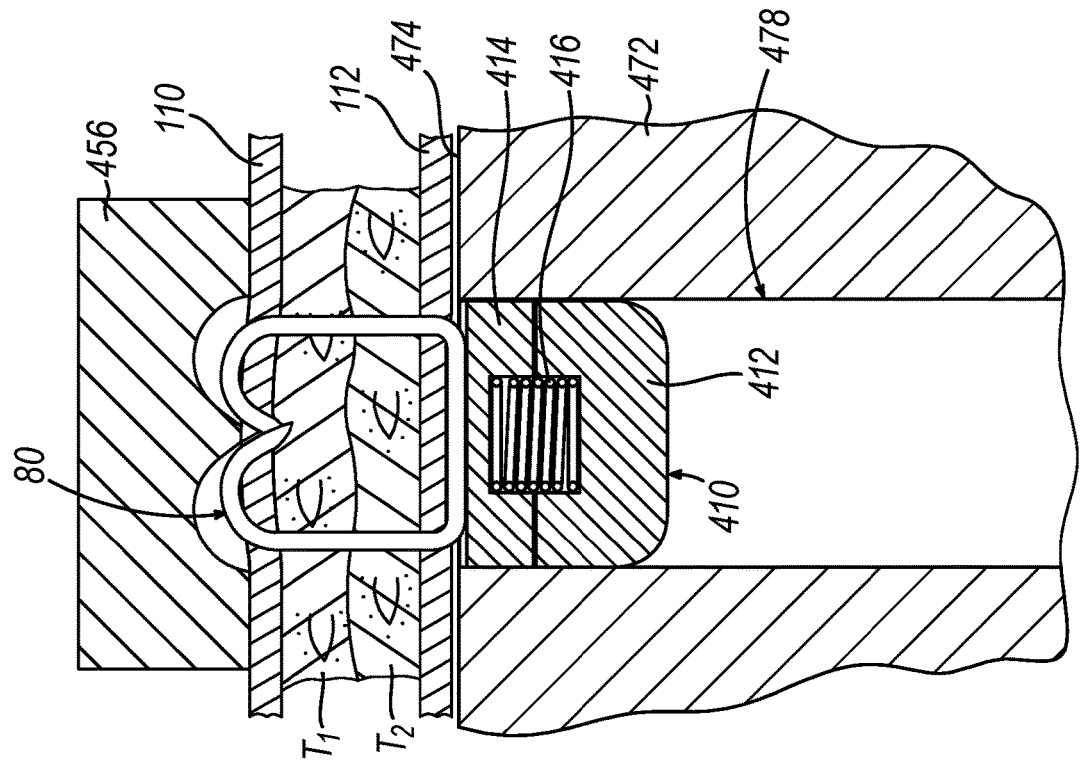
FIG. 23B depicts a cross-sectional view of a formed staple and the buttress assemblies of FIG. 22A after having been secured to the tissue having a second thickness by the end effector of FIG. 17A.
Figure 23A:
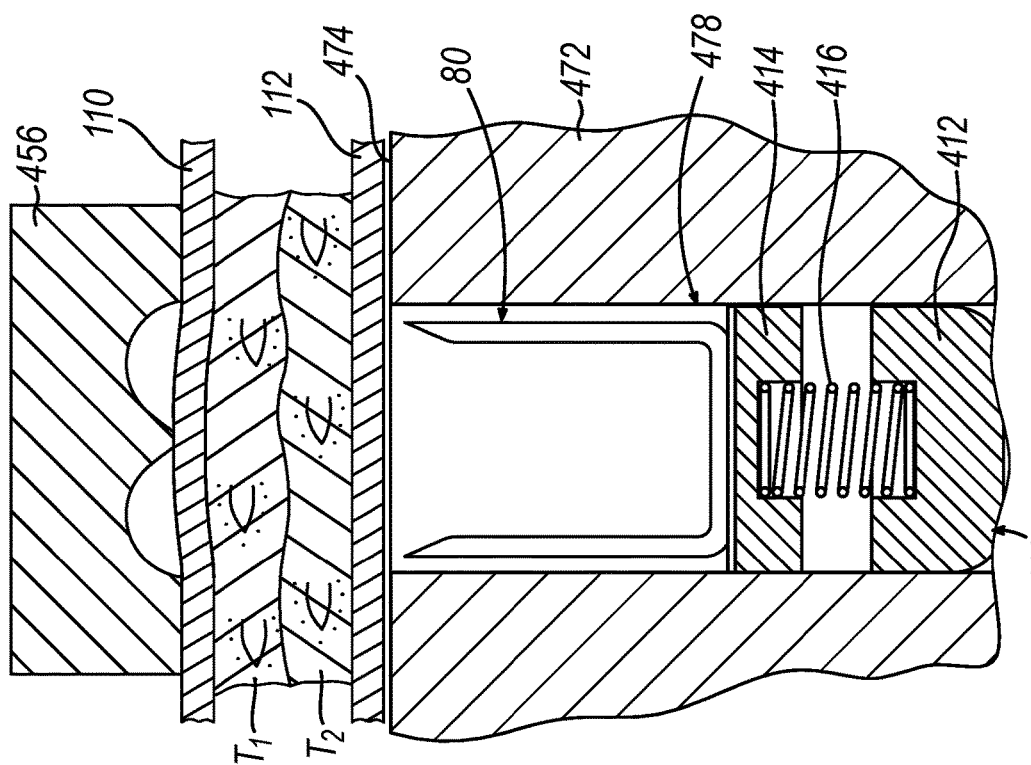
FIG. 23A depicts a cross-sectional end view of a portion of the end effector of FIG. 17A with the buttress assemblies of FIG. 7 applied to the upper and lower jaws of the end effector, showing the end effector jaws in a closed state with tissue having a second thickness positioned between the upper and lower jaws.

Conversely, FIGS. 23A-23B show compressible staple driver (410) driving a corresponding staple (80) through thicker tissue ($T_1$, $T_2$). Since the force required to drive the staple through thicker tissue ($T_1$, $T_2$) is relatively higher compared to thinner tissue, biasing body (416) does compress during the firing process. Since biasing body (416) does compress, the length of compressible staple driver (410) is reduced as compared to when in the pre-fired position. Therefore, staple driver (410) may drive staple (80) a shorter distance out of staple opening (478) as compared to when staple driver (410) is not compressed. It should also be understood that when jaws (452, 454) suitably grasp thicker tissue ($T_1$, $T_2$), the gap between the corresponding pressure loaded section (476) and anvil (456) is larger compared to when grasping thinner tissue ($T_1$, $T_2$). Therefore, with staple (80) being fired a shorter distance out of opening (478), and the gap between anvil (456) and corresponding pressure loads section (476) being larger, the final staple height of the traditional "B" formed staple may be larger in order to suitably engage thicker tissue ($T_1$, $T_2$).

It should be understood that in instances where grasped tissue ($T_1$, $T_2$) has a thickness between that shown in FIGS. 22A-23B, compressible staple driver (410) may partially compress in order to create a final staple height between those shown in FIGS. 22B and 23B.

Figure 17A:
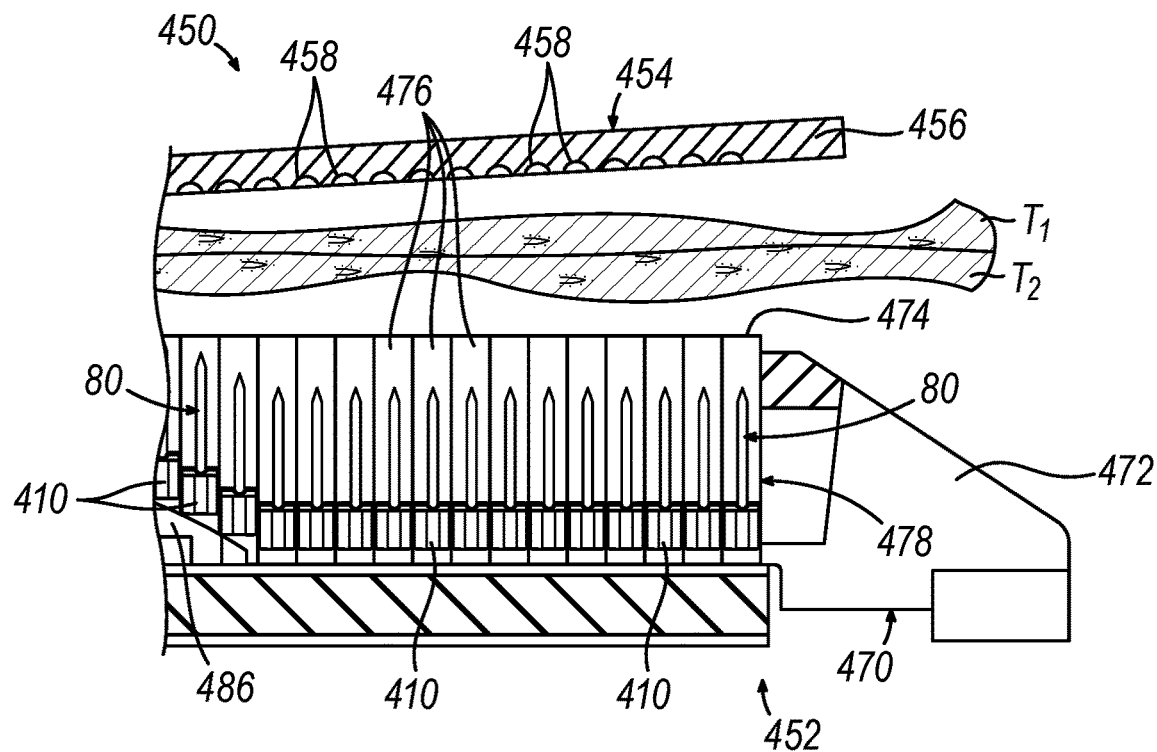
FIG. 17A depicts a side cross-sectional view of an alternative end effector with jaws in the open position.
Figure 17B:
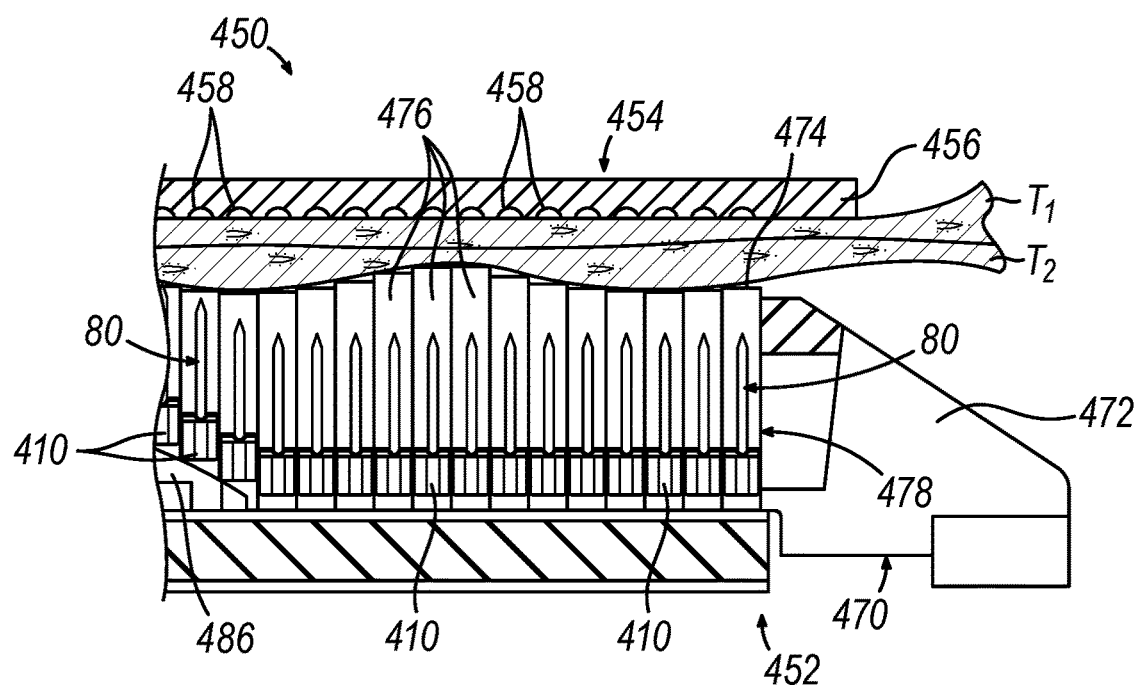
FIG. 17B depicts a side cross-sectional view of the end effector of FIG. 17A, with jaws in the closed position grasping tissue.

FIGS. 17A-17D show an exemplary use of end effector (450) to sever and staple tissue ($T_1$, $T_2$) having varying thickness along the length of end effector (450). First, as shown in FIG. 17A, jaws (452, 454) may be positioned such that tissue ($T_1$, $T_2$) is interposed between jaws (452, 454) in the open position. Next, as shown in FIG. 17B, jaws (452, 454) may suitably grasp tissue ($T_1$, $T_2$). In the current example, tissue ($T_1$, $T_2$) has varying thickness along the length of jaws (452, 454). Therefore, individual pressure loaded sections (476) of staple deck (474) may compress as shown in FIG. 17B in order to apply substantially consistent compression on the portion of tissue ($T_1$, $T_2$) grasped by jaws (452, 454).

Figure 17C:
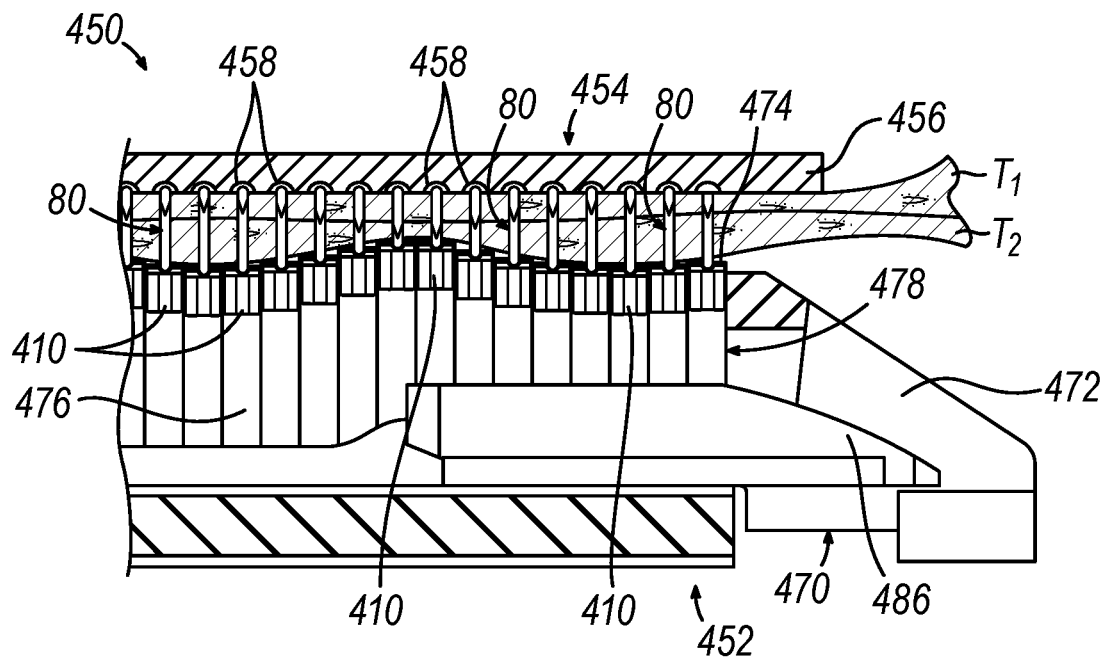
FIG. 17C depicts a side cross-sectional view of the end effector of FIG. 17A, with jaws in the closed position grasping tissue and a wedge sled of the end effector actuated distally to drive a plurality of fasteners into grasped tissue and the buttress assembly.
Figure 17D:
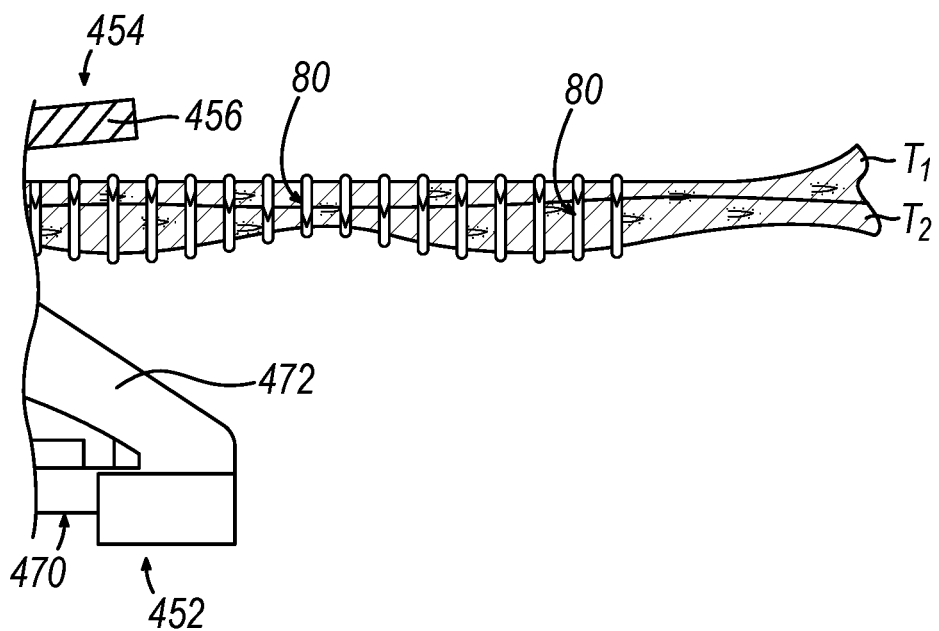
FIG. 17D depicts a side cross-sectional view of the end effector of FIG. 17A, with jaws in the open position, thereby releasing the grasped tissue and plurality of fasteners.
Figure 18:
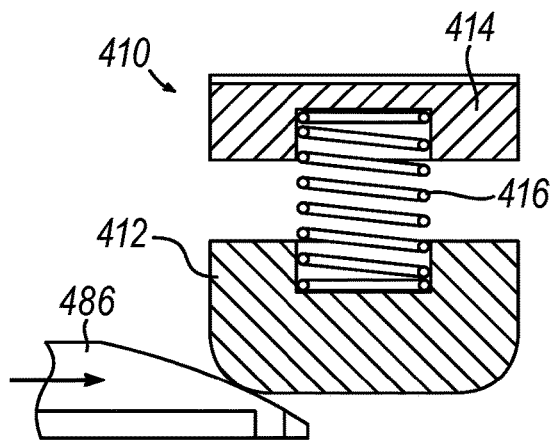
FIG. 18 depicts a side cross-sectional view of a staple driver and the wedge sled of the end effector of FIG. 17A.

Once tissue ($T_1$, $T_2$) is grasped and ready to be severed and stapled, end effector (450) may be fired in accordance with the description herein. Therefore, as shown in FIG. 17C, wedge sled (486) may be actuated distally in similar fashion as wedge sled (86) described above, thereby actuating compressible drivers (410) upward within a respective opening (478), creating traditional "B" form staples with varying staple heights in accordance with the description herein. Next, as shown in FIG. 17D, with tissue ($T_1$, $T_2$) suitably severed and stapled in accordance with the description herein, jaws (452, 454) may release tissue ($T_1$, $T_2$).

Figure 19:
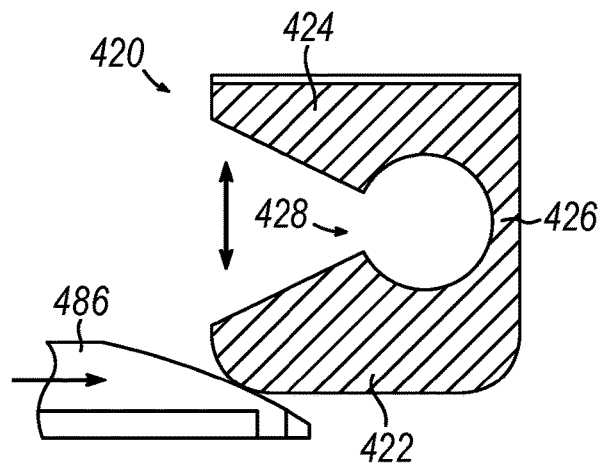
FIG. 19 depicts a side cross-sectional view of the wedge sled of the end effector of FIG. 17A and an alternative staple driver.
Figure 20:
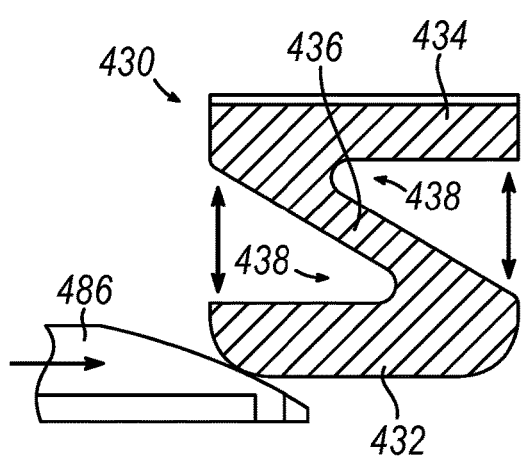
FIG. 20 depicts a side cross-sectional view of the wedge sled of the end effector of FIG. 17A and an alternative staple driver.
Figure 21:
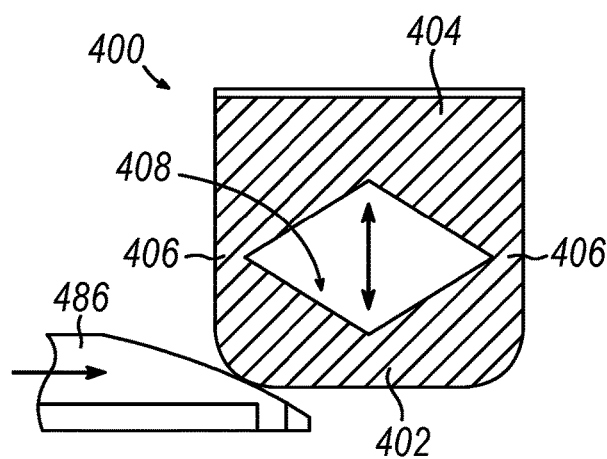
FIG. 21 depicts a side cross-sectional view of the wedge sled of the end effector of FIG. 17A and an alternative staple driver.

While the current compressible staple driver (410) includes three separate components in wedge engagement body (412), staple engagement body (414), and a biasing body (416) interposed between bodies (412, 414); this is merely optional. In some instances, a single body may be used to form a compressible staple driver. FIGS. 19-21 show various different forms in which compressible staple driver (420, 430, 400) may be formed.

FIG. 19 shows compressible staple driver (420) formed of a single body having a sled engagement portion (422), a staple endearment portion (424), and a flexing connecting member (426) extending between portions (422, 424). Flexing connecting member (426) in the current example is located on a lateral side such that compressible staple driver (420) defines a cutout (428). Cutout (428) provides a space for portions (422, 424) to flex relative to each other during exemplary use in accordance with the description herein. Flexing connecting member (426) is resiliently flexible to bend in response to compressible staple driver (420) driving a staple (80) through thicker tissue ($T_1$, $T_2$). Therefore, compressible staple driver (420) may have substantially the same functionality of staple driver (410) while being formed of a single piece of material.

FIG. 20 shows compressible staple driver (430) formed of single body having a sled engagement portion (432), a staple endearment portion (434), and a flexing connecting member (436) extending between portions (432, 434). Flexing connecting member (436) in the current example extends across different lateral sides such that compressible staple driver (430) defines two cutouts (438). Cutouts (438) provide a space for portions (432, 434) to flex relative to each other during exemplary use in accordance with the description herein. Flexing connecting member (436) is resiliently flexible to bend in response to compressible staple driver (430) driving a staple (80) through thicker tissue ($T_1$, $T_2$). Therefore, compressible staple driver (430) may have substantially the same functionality of staple driver (410) while being formed of a single piece of material.

FIG. 21 shows compressible staple driver (400) formed of single body having a sled engagement portion (402), a staple endearment portion (404), and two flexing connecting member (406) extending between portions (432, 434). Flexing connecting members (406) in the current example extends linearly on different lateral sides such that compressible staple driver (400) defines a diamond shape cutout (408). Cutout (408) provides a space for portions (402, 404) to flex relative to each other during exemplary use in accordance with the description herein. Flexing connecting members (406) are resiliently flexible to bend in response to compressible staple driver (400) driving a staple (80) through thicker tissue ($T_1$, $T_2$). Therefore, compressible staple driver (400) may have substantially the same functionality of staple driver (410) while being formed of a single piece of material.

V. Exemplary Lower Tray Having Resilient Lower Surface

Figure 24:
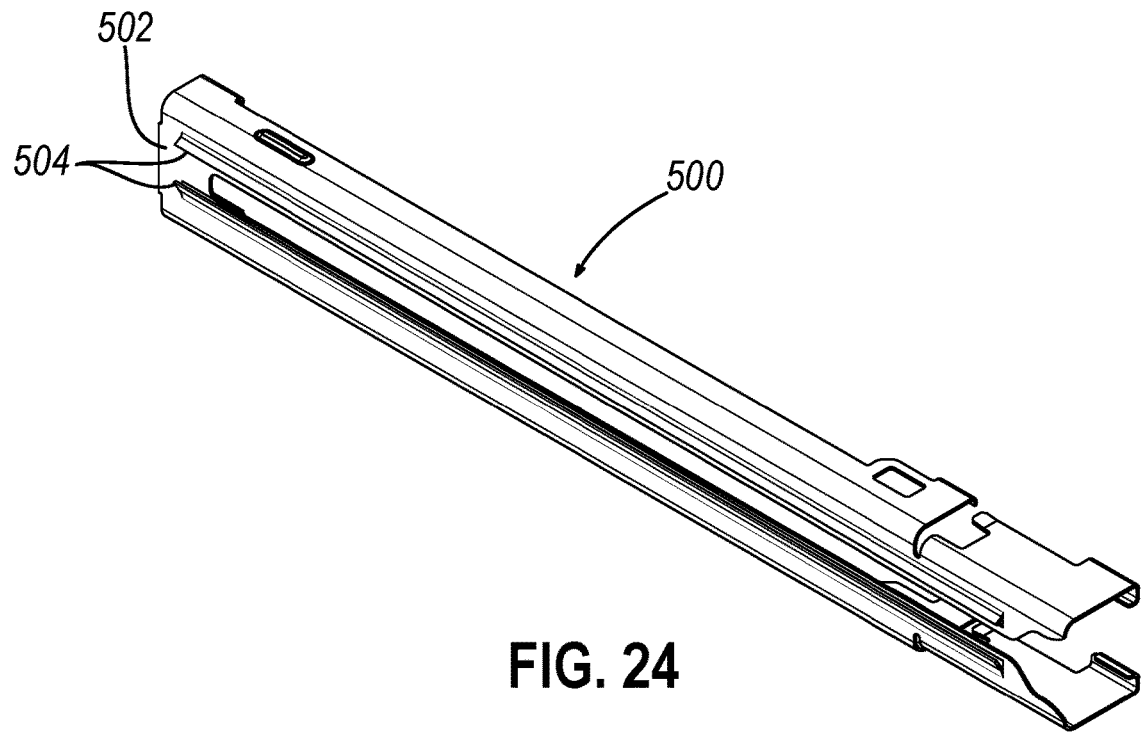
FIG. 24 depicts a perspective view of an alternative lower tray.
Figure 25:
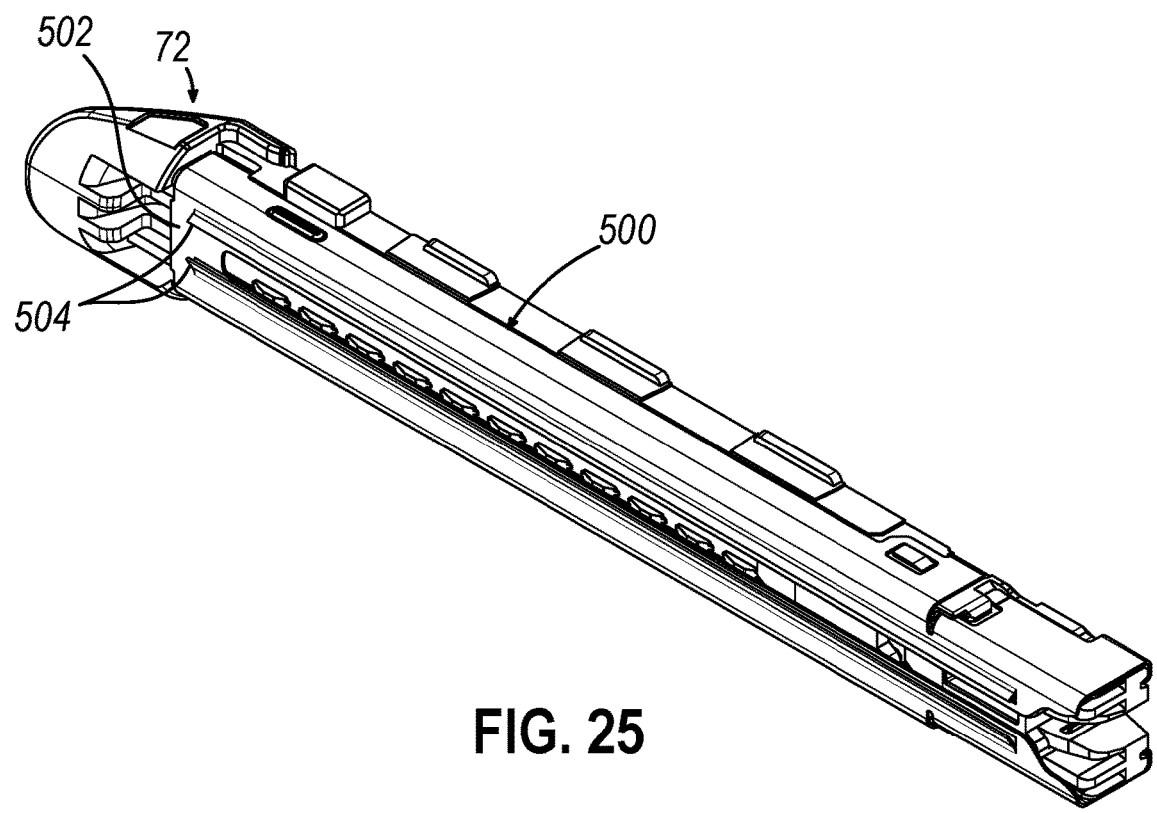
FIG. 25 depicts a perspective of the lower tray of FIG. 24 coupled with a replaceable cartridge of the end effector of FIG. 3.
Figure 26:
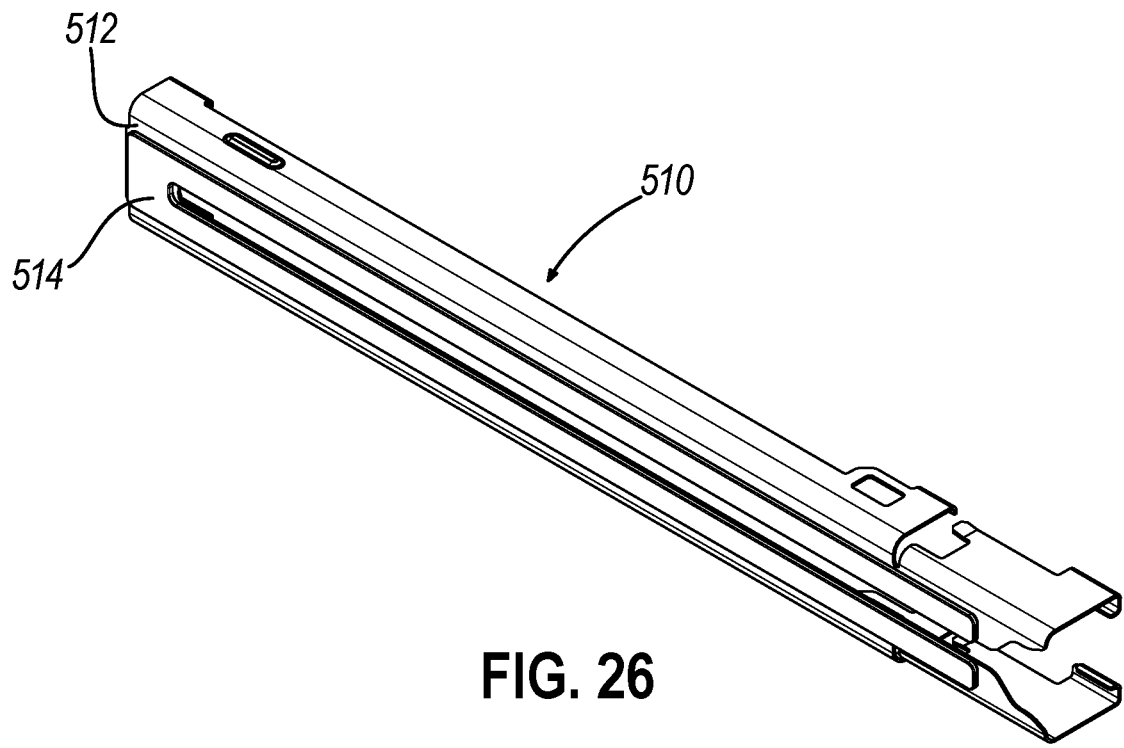
FIG. 26 depicts a perspective view of an alternative lower tray.
Figure 27:
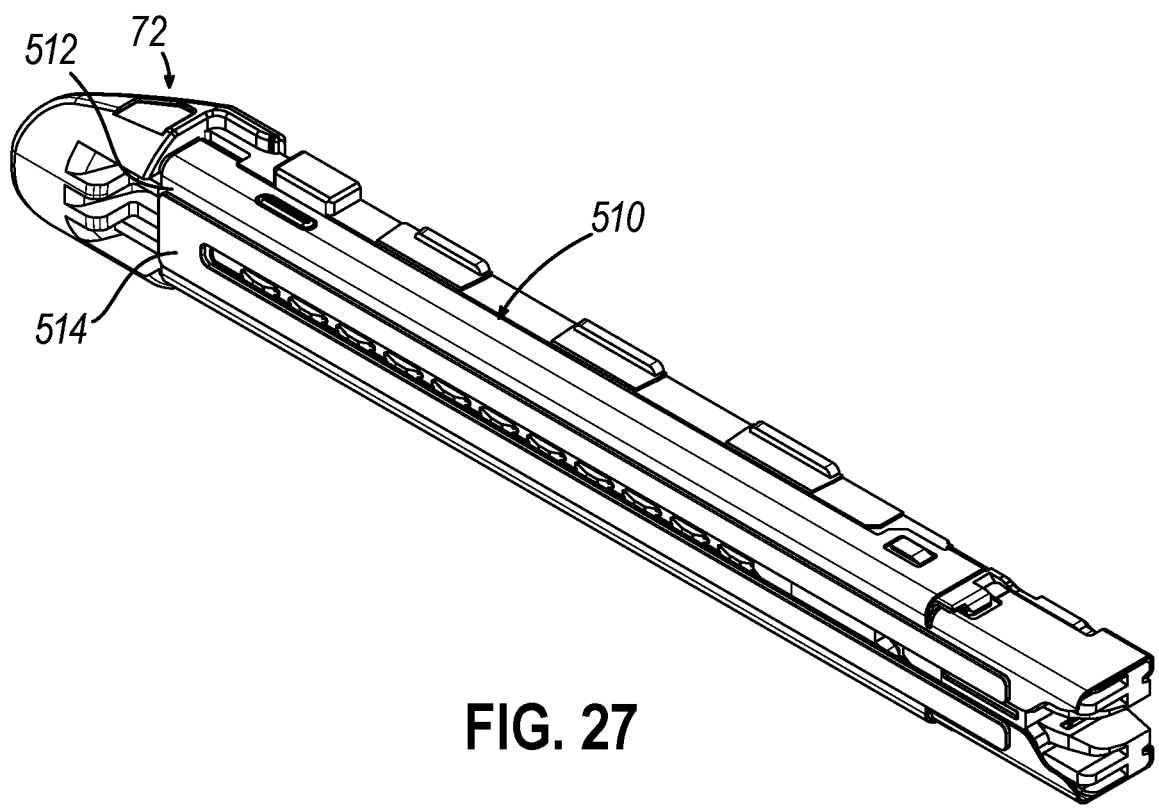
FIG. 27 depicts a perspective view of the lower tray of FIG. 26 coupled with a replaceable cartridge of the end effector of FIG. 3.

In some instances, in may be desirable to alter the distance between upwardly extending deck (74) and anvil (56) to accommodate for different tissue thicknesses without the necessary incorporation of an adjunct. FIGS. 24 and 26 show different lower trays (500, 510) that may be readily incorporated into replaceable cartridge (70), as shown in FIGS. 25 and 27, in replacement of lower tray (84) described above. Lower tray (500) includes an underside (502) that has a pair of resilient tabs (504) extending away from the rest of lower tray (500); while lower tray (510) includes an underside (512) with a compressible pad (514) extending away from the rest of lower tray (510).

Resilient tabs (504) and compressible pad (514) are each configured to engage lower jaw (52) when suitably coupled with replaceable cartridge assembly (70) such that tabs (504) and pad (514) may compress in response to jaws (52, 54) grasping thicker than normal tissue ($T_1$, $T_2$) during exemplary use. Therefore, as tabs (504) or pad (514) compress, the distances between deck (74) an anvil (56) increase. The increase in distance between deck (74) and anvil (56) may inhibit over clamping and potentially damaging thicker tissue ($T_1$, $T_2$) grasped by jaws (52, 54) during exemplary use in accordance with the description herein. Therefore, lower trays (500, 510) may be utilized in order to allow jaws (52, 54) to grasp tissue ($T_1$, $T_2$) having a range of thicknesses while inhibiting over clamping and potential damage of such tissue ($T_1$, $T_2$).

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a first jaw; (b) a second jaw, wherein the first jaw and the second jaw are configured to actuate relative to each other between an open position and a closed position; (c) a buttress assembly configured to selectively associate with the first jaw, wherein the buttress assembly comprises a compressible material; and (d) a fastener assembly associated with the second jaw, wherein the fastener assembly and the buttress assembly are configured to cooperatively grasp tissue while the first jaw and the second jaw are in the closed position, wherein the fastener assembly comprises: (i) a deck defining a plurality of openings; and (ii) a plurality of fasteners, wherein each fastener of the plurality of fasteners is housed within an opening of the plurality of openings, wherein each fastener of the plurality of fasteners is configured to actuate out of the opening and into the buttress assembly, wherein each fastener of the plurality of fasteners comprises: (A) a first leg comprising a piercing tip, and (B) an attachment feature associated with the first leg, wherein the attachment feature is operable to engage the buttress assembly to couple the first leg with the buttress assembly without bending a portion of the first leg associated with the piercing tip.

Example 2

The surgical instrument of any one or more of the preceding Examples, wherein the attachment feature comprises a first plurality of barbs.

Example 3

The surgical instrument of any one or more of the preceding Examples, wherein each fastener of the plurality of fasteners comprises a second leg.

Example 4

The surgical instrument of any one or more of the preceding Examples, wherein each fastener of the plurality of fasteners comprises a crown extending between the first leg and the second leg.

Example 5

The surgical instrument of any one or more of the preceding Examples, wherein the crown, the first leg and the second leg form a U-shape.

Example 6

The surgical instrument of any one or more of the preceding Examples, wherein the second leg comprises a second plurality of barbs.

Example 7

The surgical instrument of any one or more of the preceding Examples, wherein the first plurality of barbs and the second plurality of barbs extend downward toward the crown.

Example 8

The surgical instrument of any one or more of the preceding Examples, wherein the first plurality of barbs and the second plurality of barbs extend annularly around the first leg and the second leg, respectively.

Example 9

The surgical instrument of any one or more of the preceding Examples, wherein the buttress assembly further comprises a mesh layer coupled to the compressible material.

Example 10

The surgical instrument of any one or more of the preceding Examples, wherein the mesh layer is configured to engage the attachment feature to further promote attachment between the plurality of fasteners and the buttress assembly.

Example 11

The surgical instrument of any one or more of the preceding Examples, wherein the attachment feature and the buttress assembly are configured to chemically react in response to the attachment feature engaging the buttress assembly.

Example 12

The surgical instrument of any one or more of the preceding Examples, wherein the attachment feature and the buttress assembly are configured to cause an energy reaction.

Example 13

The surgical instrument of any one or more of the preceding Examples, further comprising a shaft assembly extending proximally from the first jaw and the second jaw.

Example 14

The surgical instrument of any one or more of the preceding Examples, further comprising a body attached to a proximal end of the shaft assembly.

Example 15

The surgical instrument of any one or more of the preceding Examples, wherein the fastener assembly comprises a cartridge.

Example 16

A surgical instrument comprising: (a) a first jaw comprising an anvil defining a plurality of staple forming pockets; (b) a second jaw, wherein the first jaw and the second jaw are configured to actuate relative to each other between an open position and a closed position; and (c) a fastener assembly associated with the second jaw, wherein the fastener assembly and the anvil are configured to cooperatively grasp tissue while the first jaw and the second jaw are in the closed position, wherein the fastener assembly comprises: (i) a deck defining a plurality of openings, (ii) a plurality of staples housed within the deck, and (iii) a plurality of compressible staple drivers configured to drive the plurality of staples out of the plurality of openings and against the plurality of staple forming pockets, wherein each compressible staple driver of the plurality of compressible staple drivers is configured to selectively compress when exerting a predetermined minimum force against the respective staple.

Example 17

The surgical instrument of any one or more of the preceding Examples, wherein each compressible staple driver comprising a driving body, a staple engagement body, and a biasing member interposed between the driving body and the staple engagement body.

Example 18

The surgical instrument of any one or more of the preceding Examples, wherein the biasing member comprises a spring.

Example 19

A surgical instrument comprising: (a) a first jaw comprising an anvil defining a plurality of staple forming pockets; (b) a second jaw, wherein the first jaw and the second jaw are configured to actuate relative to each other between an open position and a closed position; and (c) a fastener assembly associated with the second jaw, wherein the fastener assembly and the anvil are configured to cooperatively grasp tissue while the first jaw and the second jaw are in the closed position, wherein the fastener assembly comprises: (i) a plurality of pressure loaded sections forming a deck, wherein each pressure loaded section defines a respective staple opening, wherein each pressure loaded section is configured to vary in height in response to a clamping force generated while the cartridge assembly and the anvil cooperatively grasp tissue, and (ii) a plurality of staples housed within the staple openings.

Example 20

The surgical instrument of any one or more of the preceding Examples, wherein each pressure loaded section of the plurality of pressure loaded sections comprises a resilient feature configured to exert a resilient force on a respective section of tissue.

VII. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/704,075, entitled "Tissue Cushion Adjuncts for Surgical Stapler End Effector," filed Mar. 25, 2022, published as U.S. Pat. Pub. No. 2023/0301656 on Sep. 28, 2023; U.S. patent application Ser. No. 17/704,079, entitled "Tissue Cushion Adjunct for Surgical Stapler End Effector," filed on Mar. 25, 2022, published as U.S Pat. Pub. No. 2023/0301674 on Sep. 28, 2023; U.S. patent application Ser. No. 17,704,082, entitled "Thermally Formed Tissue Cushion Adjunct for Surgical Stapler End Effector," filed Mar. 25, 2022, published as U.S. Pat. Pub. No. 2023/0301657 on Sep. 28, 2023; and U.S. patent applicaiton Ser. No. 17/704,083, entitled "Tissue Cushion Adjunct With Staple Leg Support Features for Surgical Stapler End Effector," filed on Mar. 25, 2022, published as U.S. Pat. Pub. No. 2023/0320742 on Oct. 12, 2023. The disclosure of each of these U.S. patent references is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a first jaw;
   (b) a second jaw, wherein the first jaw and the second jaw are configured to actuate relative to each other between an open position and a closed position;
   (c) a buttress configured to selectively associate with the first jaw, wherein the buttress comprises a compressible material configured to compress, wherein the buttress comprises a plurality of internal fasteners; and
   (d) a cartridge associated with the second jaw, wherein the cartridge and the buttress are configured to cooperatively grasp tissue varying in thickness while the first jaw and the second jaw are in the closed position such that the compressible material of the buttress is configured to compress into a complementary profile relative to the tissue varying in thickness, wherein the cartridge comprises:
      (i) a deck defining a plurality of openings; and
      (ii) a plurality of fasteners, wherein each fastener of the plurality of fasteners is housed within an opening of the plurality of openings, wherein each fastener of the plurality of fasteners is configured to actuate out of the opening and into the buttress, wherein each fastener of the plurality of fasteners comprises:
         (A) a first leg comprising a piercing tip, and
         (B) an attachment feature associated with the first leg, wherein the attachment feature is operable to engage the buttress to couple the first leg with the buttress without bending a portion of the first leg associated with the piercing tip and such that the compressible material maintains the complementary profile relative to the tissue varying in thickness,
      wherein at least one internal fastener of the plurality of internal fasteners is configured to pierce tissue in response to the cartridge and the buttress cooperatively grasping tissue.

2. The surgical instrument of claim 1, wherein the attachment feature comprises a first plurality of barbs.

3. The surgical instrument of claim 2, wherein each fastener of the plurality of fasteners comprises a second leg.

4. The surgical instrument of claim 3, wherein each fastener of the plurality of fasteners comprises a crown extending between the first leg and the second leg.

5. The surgical instrument of claim 4, wherein the crown, the first leg and the second leg form a U-shape.

6. The surgical instrument of claim 5, wherein the second leg comprises a second plurality of barbs.

7. The surgical instrument of claim 6, wherein the first plurality of barbs and the second plurality of barbs extend downward toward the crown.

8. The surgical instrument of claim 6, wherein the first plurality of barbs and the second plurality of barbs extend annularly around the first leg and the second leg, respectively.

9. The surgical instrument of claim 1, wherein the buttress further comprises a mesh layer coupled to the compressible material.

10. The surgical instrument of claim 9, wherein the mesh layer is configured to engage the attachment feature to further promote attachment between the plurality of fasteners and the buttress.

11. The surgical instrument of claim 1, wherein the attachment feature and the buttress are configured to chemically react in response to the attachment feature engaging the buttress.

12. The surgical instrument of claim 1, wherein the attachment feature and the buttress are configured to cause an energy reaction.

13. The surgical instrument of claim 1, further comprising a shaft assembly extending proximally from the first jaw and the second jaw.

14. The surgical instrument of claim 13, further comprising a body attached to a proximal end of the shaft assembly.

15. The surgical instrument of claim 1, wherein the cartridge comprises a replaceable cartridge body configured to selectively attach to the second jaw.

16. A surgical instrument comprising:
   (a) a first jaw;
   (b) a second jaw, wherein the first jaw and the second jaw are configured to actuate relative to each other between an open position and a closed position;
   (c) a buttress configured to selectively associate with the first jaw, wherein the buttress comprises a compressible material and a first plurality of fasteners housed within the compressible material; and
   (d) a cartridge associated with the second jaw, wherein the cartridge and the buttress are configured to cooperatively grasp tissue while the first jaw and the second jaw are in the closed position, wherein the cartridge comprises:
      (i) a deck defining a plurality of openings; and
      (ii) a second plurality of fasteners, wherein each fastener of the second plurality of fasteners is housed within an opening of the plurality of openings, wherein each fastener of the second plurality of fasteners is configured to actuate out of the opening and into the buttress, wherein each fastener of the second plurality of fasteners comprises:
         (A) a first leg comprising a piercing tip, and
         (B) at least one barb associated with the first leg, wherein the at least one barb is operable to engage the buttress to couple the first leg with the buttress without bending a portion of the first leg associated with the piercing tip,
      wherein at least one fastener of the first plurality of fasteners is configured to pierce tissue in response to the cartridge and the buttress cooperatively gasping tissue while the first jaw and the second jaw are in the closed position.

17. A surgical instrument comprising:
   (a) a first jaw;
   (b) a second jaw, wherein the first jaw and the second jaw are configured to actuate relative to each other between an open position and a closed position;
   (c) a buttress configured to selectively associate with the first jaw, wherein the buttress comprises a compressible material, wherein the buttress comprises at least one internal fastener housed within the compressible material; and (d) a cartridge associated with the second jaw, wherein the cartridge and the buttress are configured to cooperatively grasp tissue while the first jaw and the second jaw are in the closed position, wherein the cartridge comprises:

(i) a deck defining a plurality of openings; and (ii) a plurality of fasteners, wherein each fastener of the plurality of fasteners is housed within an opening of the plurality of openings, wherein each fastener of the plurality of fasteners is configured to actuate out of the opening and into the buttress, wherein each fastener of the plurality of fasteners comprises:

(A) a first leg comprising a piercing tip, and (B) at least one barb associated with the first leg, wherein the at least one barb is operable to engage the buttress to couple the first leg with the buttress without bending a portion of the first leg associated with the piercing tip, wherein the at least one internal fastener is configured to pierce tissue in response to the cartridge and the buttress cooperatively grasping tissue.

18. The surgical instrument of claim 17, wherein the compressible material comprises a first thickness at the proximal end of the first jaw and a second thickness at the distal end of the first jaw, wherein the second thickness is greater than the first thickness.

* * * * *